United States Patent
Raines et al.

(10) Patent No.: US 12,168,042 B2
(45) Date of Patent: Dec. 17, 2024

(54) CIRCULAR STRAINED ZYMOGEN COMPOSITIONS AND METHODS OF USE

(71) Applicants: Massachusetts Institute of Technology, Cambridge, MA (US); Wisconsin Alumni Research Foundation, Madison, WI (US)

(72) Inventors: Ronald Raines, Cambridge, MA (US); Ian Windsor, Brighton, MA (US)

(73) Assignees: Massachusetts Institute of Technology, Cambridge, MA (US); Wisconsin Alumni Research Foundation, Madison, WI (US)

( * ) Notice: Subject to any disclaimer, the term of this patent is extended or adjusted under 35 U.S.C. 154(b) by 369 days.

(21) Appl. No.: 16/913,924

(22) Filed: Jun. 26, 2020

(65) Prior Publication Data

US 2020/0405829 A1    Dec. 31, 2020

Related U.S. Application Data

(60) Provisional application No. 62/868,841, filed on Jun. 28, 2019.

(51) Int. Cl.
  *C12N 9/22* (2006.01)
  *A61K 38/55* (2006.01)

(52) U.S. Cl.
  CPC .............. *A61K 38/55* (2013.01); *C12N 9/22* (2013.01)

(58) Field of Classification Search
  CPC .................................. A61K 38/55; C12N 9/22
  See application file for complete search history.

(56) References Cited

U.S. PATENT DOCUMENTS

| | | | |
|---|---|---|---|
| 2004/0063116 A1* | 4/2004 | Raines ..................... | C12N 9/22 435/5 |
| 2011/0118330 A1* | 5/2011 | Ghosh .................. | C07D 313/14 549/372 |

FOREIGN PATENT DOCUMENTS

JP            2011200226 A  * 10/2011  .............. C12Q 1/37

OTHER PUBLICATIONS

Bowie et al, "Deciphering the message in protein sequences: tolerance to amino acid substitutions," Science 247:1306-1310 (1990) ) (Year: 1990).*
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol. 111:2129-2138 (1990) (Year: 1990).*
English machine translation of JP2011-200226A. 18 pages, accessed at JPO Dec. 31, 2022. (Year: 2011).*
International Preliminary Report on Patentability mailed Jan. 6, 2022, for Application No. PCT/US2020/039910.
International Search Report and Written Opinion for PCT/US2020/039910, mailed on Oct. 15, 2020.
Bal et al., Human pancreatic ribonuclease—deletion of the carboxyl-terminal EDST extension enhances ribonuclease activity and thermostability. Eur J Biochem. Apr. 15, 1997;245(2):465-9. doi: 10.1111/j.1432-1033.1997.t01-1-00465.x. PMID: 9151980.
Beck et al., Identification of efficiently cleaved substrates for HIV-1 protease using a phage display library and use in inhibitor development. Virology. Sep. 1, 2000;274(2):391-401. doi: 10.1006/viro.2000.0420.
Butler et al., Structural and thermodynamic analysis of a conformationally strained circular permutant of barnase. Biochemistry. Apr. 21, 2009;48(15):3497-507. doi: 10.1021/bi900039e. PMID: 19260676; PMCID: PMC2756614.
Callís et al., Towards tricking a pathogen's protease into fighting infection: the 3D structure of a stable circularly permuted onconase variant cleavedby HIV-1 protease. PLoS One. 2013;8(1):e54568. doi: 10.1371/journal.pone.0054568. Epub Jan. 18, 2013. PMID: 23349931; PMCID: PMC3548804.
Chun et al., Rebound of plasma viremia following cessation of antiretroviral therapy despite profoundly low levels of HIV reservoir: implications for eradication. AIDS. Nov. 27, 2010;24(18):2803-8. doi: 10.1097/QAD.0b013e328340a239. PMID: 20962613; PMCID: PMC3154092.
Eller et al., Bovine brain ribonuclease is the functional homolog of human ribonuclease 1. J Biol Chem. Sep. 19, 2014;289(38):25996-26006. doi: 10.1074/jbc.M114.566166. Epub Jul. 30, 2014. PMID: 25078100; PMCID: PMC4176206.
Evans et al., Protein trans-splicing and cyclization by a naturally split intein from the dnaE gene of *Synechocystis* species PCC6803. J Biol Chem. Mar. 31, 2000;275(13):9091-4. doi: 10.1074/jbc.275.13.9091. PMID: 10734038.
Fisher et al., Coulombic forces in protein-RNA interactions: binding and cleavage by ribonuclease A and variants at Lys7, Arg10, and Lys66. Biochemistry. Sep. 1, 1998;37(35):12121-32. doi: 10.1021/bi9807431. PMID: 9724524.
Fontecilla-Camps et al., Crystal structure of ribonuclease A.d(ApTpApApG) complex. Direct evidence for extended substrate recognition. J Biol Chem. Aug. 26, 1994;269(34):21526-31. doi: 10.2210/pdblrcn/pdb. PMID: 8063789.
Fujii et al., Significance of the four carboxyl terminal amino acid residues of bovine pancreatic ribonuclease A for structural folding. J Biochem. Feb. 2002;131(2):193-200. doi: 10.1093/oxfordjournals.jbchem.a003087. PMID: 11820931.
Gront et al., Generalized fragment picking in Rosetta: design, protocols and applications. PLoS One. 2011;6(8):e23294. doi: 10.1371/journal.pone.0023294. Epub Aug. 24, 2011. PMID: 21887241; PMCID: PMC3160850.

(Continued)

*Primary Examiner* — Julie Ha
*Assistant Examiner* — Kristina M Hellman
(74) *Attorney, Agent, or Firm* — Wolf, Greenfield & Sacks, P.C.

(57) ABSTRACT

Disclosed herein are circular zymogens of RNase 1 that have a proteolytic cleavage site and are activated by a specific protease. These circular zymogens are useful for treatment of disorders that are characterized by a specific protease (e.g., HTV-1 protease).

14 Claims, 6 Drawing Sheets

Specification includes a Sequence Listing.

(56) References Cited

OTHER PUBLICATIONS

Hendrickson et ql., "My future is bright . . . I won't die with the cause of AIDS": ten-year patient ART outcomes and experiences in South Africa. J Int AIDS Soc. Oct. 2018;21(10):e25184. doi: 10.1002/jia2.25184. PMID: 30318848; PMCID: PMC6186968.
HIV-Causal Collaboration et al., The effect of combined antiretroviral therapy on the overall mortality of HIV-infected individuals. AIDS. Jan. 2, 2010;24(1):123-37. doi: 10.1097/QAD.0b013e3283324283. PMID: 19770621; PMCID: PMC2920287.
Johnson et al., A ribonuclease zymogen activated by the NS3 protease of the hepatitis C virus. FEBS J. Dec. 2006;273(23):5457-65. doi: 10.1111/j.1742-4658.2006.05536.x. PMID: 17116245.
Johnson et al., Cytotoxic ribonucleases: the dichotomy of Coulombic forces. Biochemistry. Sep. 11, 2007;46(36):10308-16. doi: 10.1021/bi700857u. Epub Aug. 18, 2007. PMID: 17705507; PMCID: PMC2864629.
Johnson et al., Inhibition of human pancreatic ribonuclease by the human ribonuclease inhibitor protein. J Mol Biol. Apr. 27, 2007;368(2):434-49. doi: 10.1016/j.jmb.2007.02.005. Epub Feb. 9, 2007. PMID: 17350650; PMCID: PMC1993901.
Kanno et al., luciferase for real-time sensing of caspase-3 activities in living mammals. Angew Chem Int Ed Engl. 2007;46(40):7595-9. doi: 10.1002/anie.200700538. PMID: 17722214.
Kelemen et al., Hypersensitive substrate for ribonucleases. Nucleic Acids Res. Sep. 15, 1999;27(18):3696-701. doi: 10.1093/nar/27.18.3696. PMID: 10471739; PMCID: PMC148625.
Kim et al., Getting the "Kill" into "Shock and Kill": Strategies to Eliminate Latent HIV. Cell Host Microbe. Jan. 10, 2018;23(1):14-26. doi: 10.1016/j.chom.2017.12.004. PMID: 29324227; PMCID: PMC5990418.
Leland et al., Endowing human pancreatic ribonuclease with toxicity for cancer cells. J Biol Chem. Nov. 16, 2001;276(46):43095-102. doi: 10.1074/jbc.M106636200. Epub Sep. 12, 2001. PMID: 11555655.
Lomax et al., Rational design and evaluation of mammalian ribonuclease cytotoxins. Methods Enzymol. 2012;502:273-90. doi: 10.1016/8978-0-12-416039-2.00014-8. PMID: 22208989; PMCID: PMC3304445.
O'Meara et al., Combined covalent-electrostatic model of hydrogen bonding improves structure prediction with Rosetta. J Chem Theory Comput. Feb. 10, 2015;11(2):609-22. doi: 10.1021/ct500864r. PMID: 25866491; PMCID: PMC4390092.
Plainkum et al., Creation of a zymogen. Nat Struct Biol. Feb. 2003;10(2):115-9. doi: 10.1038/nsb884. PMID: 12496934; PMCID: PMC2819095.
Pous et al., Three-dimensional structure of human RNase 1 delta N7 at 1.9 A resolution. Acta Crystallogr D Biol Crystallogr. Apr. 2001;57(Pt 4):498-505. doi: 10.1107/s0907444901001147. PMID: 11264578.
Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011. PMID: 21656885; PMCID: PMC3230118.
Shirakawa et al., Reactivation of latent HIV by histone deacetylase inhibitors. Trends Microbiol. Jun. 2013;21(6):277-85. doi: 10.1016/j.tim.2013.02.005. Epub Mar. 18, 2013. PMID: 23517573; PMCID: PMC3685471.
Siliciano et al., HIV latency. Cold Spring Harb Perspect Med. Sep. 2011;1(1):a007096. doi: 10.1101/cshperspect.a007096. PMID: 22229121; PMCID: PMC3234450.
Stein et al., Improvements to robotics-inspired conformational sampling in rosetta. PLoS One. May 21, 2013;8(5):e63090. doi: 10.1371/journal.pone.0063090. PMID: 23704889; PMCID: PMC3660577.
Stratton et al., Converting a protein into a switch for biosensing and functional regulation. Protein Sci. Jan. 2011;20(1):19-29. doi: 10.1002/pro.541. PMID: 21064163; PMCID: PMC3047058.
Tözsér et al., Comparison of the HIV-1 and HIV-2 proteinases using oligopeptide substrates representing cleavage sites in Gag and Gag-Pol polyproteins. FEBS Lett. Apr. 9, 1991;281(1-2):77-80. doi: 10.1016/0014-5793(91)80362-7. PMID: 2015912.
Turcotte et al., Design and characterization of an HIV-specific ribonuclease zymogen. AIDS Res Hum Retroviruses. Nov. 2008;24(11):1357-63. doi: 10.1089/aid.2008.0146. PMID: 19025416; PMCID: PMC2888699.
Vila-Perelló et al., Biological applications of protein splicing. Cell. Oct. 15, 2010;143(2):191-200. doi: 10.1016/j.cell.2010.09.031. PMID: 20946979; PMCID: PMC3004290.
Vocero-Akbani et al., Killing HIV-infected cells by transduction with an HIV protease-activated caspase-3 protein. Nat Med. Jan. 1999;5(1):29-33. doi: 10.1038/4710. PMID: 9883836.
Wang et al., Protein-protein docking with backbone flexibility. J Mol Biol. Oct. 19, 2007;373(2):503-19. doi: 10.1016/j.jmb.2007.07.050. Epub Aug. 2, 2007. PMID: 17825317.
Windsor et al., A substrate selected by phage display exhibits enhanced side-chain hydrogen bonding to HIV-1 protease. Acta Crystallogr D Struct Biol. Jul. 1, 2018;74(Pt 7):690-694. doi: 10.1107/S2059798318006691. Epub Jun. 27, 2018. PMID: 29968678; PMCID: PMC6038388.
Windsor et al., Circular zymogens of human ribonuclease 1. Protein Sci. Sep. 2019;28(9):1713-1719. doi: 10.1002/pro.3686. Epub Aug. 6, 2019. PMID: 31306518; PMCID: PMC6699097.
Windsor et al., Fluorogenic Assay for Inhibitors of HIV-1 Protease with Sub-picomolar Affinity. Sci Rep. Aug. 11, 2015;5:11286. doi: 10.1038/srep11286. PMID: 26261098; PMCID: PMC4531283.
Yu et al., Circular permutation: a different way to engineer enzyme structure and function. Trends Biotechnol. Jan. 2011;29(1):18-25. doi: 10.1016/j.tibtech.2010.10.004. Epub Nov. 17, 2010. PMID: 21087800.
Zettler et al., The naturally split Npu DnaE intein exhibits an extraordinarily high rate in the protein trans-splicing reaction. FEBS Lett. Mar. 4, 2009;583(5):909-14. doi: 10.1016/j.febslet.2009.02.003. Epub Feb. 10, 2009. PMID: 19302791.

\* cited by examiner

SEQUENCE LISTING

<160> NUMBER OF SEQ ID NOS: 50

<210> SEQ ID NO 1
<211> LENGTH: 8
<212> TYPE: PRT

```
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (4)..(5)
<223> OTHER INFORMATION: Cleavage site

<400> SEQUENCE: 1

Ser Gly Ile Phe Leu Glu Thr Ser
1               5

<210> SEQ ID NO 2
<211> LENGTH: 128
<212> TYPE: PRT
<213> ORGANISM: Artificial Sequence
<220> FEATURE:
<223> OTHER INFORMATION: Synthetic polypeptide

<400> SEQUENCE: 2

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
            20                  25                  30

Arg Asn Met Thr Gln Gly Arg Cys Lys Pro Val Asn Thr Phe Val His
        35                  40                  45

Glu Pro Leu Val Asp Val Gln Met Val Cys Phe Gln Glu Lys Val Thr
    50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Gly Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
        115                 120                 125

<210> SEQ ID NO 3
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 3

Lys Glu Ser Arg
1

<210> SEQ ID NO 4
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 4

Lys Glu Ser Arg Ala
1               5

<210> SEQ ID NO 5
<211> LENGTH: 6
<212> TYPE: PRT
<213> ORGANISM: Artificial Sequence
<220> FEATURE:
```

```
<223> OTHER INFORMATION: Synthetic polypeptide

<400> SEQUENCE: 5

Lys Glu Ser Arg Ala Lys
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 6

Glu Asp Ser Thr
1

<210> SEQ ID NO 7
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 7

Val Glu Asp Ser Thr
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 8

Ser Val Glu Asp Ser Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (5)..(6)
<223> OTHER INFORMATION: Cleavage site

<400> SEQUENCE: 9

Lys Pro Ile Glu Phe Leu Glu Leu Lys
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 10

Lys Pro Ile Glu Phe
1               5

<210> SEQ ID NO 11
<211> LENGTH: 4
```

```
<212> TYPE: PRT
<213> ORGANISM: Artificial Sequence
<220> FEATURE:
<223> OTHER INFORMATION: Synthetic polypeptide

<400> SEQUENCE: 11

Leu Glu Leu Lys
1

<210> SEQ ID NO 12
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (5)..(6)
<223> OTHER INFORMATION: Cleavage site

<400> SEQUENCE: 12

Thr Ala Thr Ile Met Met Gln Arg Gly Asn
1               5                   10

<210> SEQ ID NO 13
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 13

Thr Ala Thr Ile Met
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 14

Met Gln Arg Gly Asn
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (6)..(7)
<223> OTHER INFORMATION: Cleavage site

<400> SEQUENCE: 15

Glu Asp Val Val Cys Cys Ser Met Ser Tyr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
```

```
<222> LOCATION: (6)..(7)
<223> OTHER INFORMATION: Cleavage site

<400> SEQUENCE: 16

Glu Asp Val Val Ala Cys Ser Met Ser Tyr
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (4)..(5)
<223> OTHER INFORMATION: Cleavage site

<400> SEQUENCE: 17

Ala Val Leu Gln Ser Gly Phe Arg
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (4)..(5)
<223> OTHER INFORMATION: Cleavage site

<400> SEQUENCE: 18

Ala Val Leu Gln Ser Gly Phe Arg
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (4)..(5)
<223> OTHER INFORMATION: Cleavage site

<400> SEQUENCE: 19

Ala Thr Leu Gln Ser Gly Asn Ala
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (3)..(4)
<223> OTHER INFORMATION: Cleavage site

<400> SEQUENCE: 20

Pro Leu Gly Leu Ala Gly
1               5

<210> SEQ ID NO 21
<211> LENGTH: 8
```

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (4)..(5)
<223> OTHER INFORMATION: Cleavage site

<400> SEQUENCE: 21

Ile Pro Val Ser Leu Arg Ser Gly
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (5)..(6)
<223> OTHER INFORMATION: Cleavage site

<400> SEQUENCE: 22

Pro Pro Val Ile Leu Pro Ile Gln Ala
1               5

<210> SEQ ID NO 23
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 23

Gly Gly Gly Ser Gly Ile Phe Leu Glu Thr Ser Gly Gly Gly
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 24

Gly Gly Ser Gly Ile Phe Leu Glu Thr Ser Gly Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 25

Gly Ser Gly Ile Phe Leu Glu Thr Ser Gly
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
```

```
<222> LOCATION: (5)..(6)
<223> OTHER INFORMATION: Cleavage site

<400> SEQUENCE: 26

Gly Ser Gly Ile Phe Leu Glu Thr Ser Leu
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (5)..(6)
<223> OTHER INFORMATION: Cleavage site

<400> SEQUENCE: 27

Gly Ser Gly Val Phe Val Glu Thr Ser Leu
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (7)..(8)
<223> OTHER INFORMATION: Cleavage site

<400> SEQUENCE: 28

Ser Gly Gly Ser Gly Val Tyr His Val Ser Thr Leu Val Pro Glu Phe
1               5                   10                  15

<210> SEQ ID NO 29
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (5)..(6)
<223> OTHER INFORMATION: Cleavage site

<400> SEQUENCE: 29

Gly Ser Gly Val Phe Val Glu Met Pro Leu
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (7)..(8)
<223> OTHER INFORMATION: Cleavage site

<400> SEQUENCE: 30

Ser Gly Gly Ser Gly Val Phe Val Val Asn Gly Leu Val Pro Glu Phe
1               5                   10                  15

<210> SEQ ID NO 31
<211> LENGTH: 10
```

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (5)..(6)
<223> OTHER INFORMATION: Cleavage site

<400> SEQUENCE: 31

Gly Ser Gly Asn Tyr Leu Val Thr Ser Leu
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (5)..(6)
<223> OTHER INFORMATION: Cleavage site

<400> SEQUENCE: 32

Gly Ser Gly Val Tyr Leu Ala Thr Asp Leu
1               5                   10

<210> SEQ ID NO 33
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (7)..(8)
<223> OTHER INFORMATION: Cleavage site

<400> SEQUENCE: 33

Ser Gly Gly Ser Gly Ile Met Phe Glu Ser Asn Leu Val Pro Glu Phe
1               5                   10                  15

<210> SEQ ID NO 34
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (5)..(6)
<223> OTHER INFORMATION: Cleavage site

<400> SEQUENCE: 34

Gly Ser Gly Ile Met Phe Gln Ser Ala Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (5)..(6)
<223> OTHER INFORMATION: Cleavage site
```

```
<400> SEQUENCE: 35

Gly Ser Gly Asn Tyr Phe Val Gln Gly Leu
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (5)..(6)
<223> OTHER INFORMATION: Cleavage site

<400> SEQUENCE: 36

Gly Ser Gly Asn Tyr Phe Val Glu Thr Leu
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (5)..(6)
<223> OTHER INFORMATION: Cleavage site

<400> SEQUENCE: 37

Ile Arg Lys Ile Leu Phe Leu Asp Gly
1               5

<210> SEQ ID NO 38
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (5)..(6)
<223> OTHER INFORMATION: Cleavage site

<400> SEQUENCE: 38

Val Ser Gln Asn Tyr Pro Ile Val Gln Asn
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (5)..(6)
<223> OTHER INFORMATION: Cleavage site

<400> SEQUENCE: 39

Gly Ser Gly Leu Phe Thr Glu Tyr Gly Leu
1               5                   10

<210> SEQ ID NO 40
<211> LENGTH: 18
<212> TYPE: PRT
<213> ORGANISM: Artificial Sequence
```

```
<220> FEATURE:
<223> OTHER INFORMATION: Synthetic polypeptide

<400> SEQUENCE: 40

His Phe Asp Ala Ser Val Lys Glu Thr Ala Ala Ala Lys Phe Glu Arg
1               5                   10                  15

Gln His

<210> SEQ ID NO 41
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 41

His Phe Asp Ala Ser Val Gly Ser Thr Ala Thr Ile Met Met Gln Arg
1               5                   10                  15

Gly Asn Ala Gly Lys Glu Thr Ala Ala Ala Lys Phe Glu Arg Gln His
            20                  25                  30

<210> SEQ ID NO 42
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 42

Gly His Asp Ala Ser Val Glu Asp Ser Thr Lys Glu Ser Arg Ala Lys
1               5                   10                  15

Lys Phe Gln Arg Gln His
            20

<210> SEQ ID NO 43
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 43

His Gly Asp Ala Ser Val Gly Gly Ser Gly Ile Phe Leu Glu Thr
1               5                   10                  15

Ser Gly Gly Gly Lys Glu Ser Arg Ala Lys Lys Phe Gln Arg Gln His
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 44

His Phe Asp Ala Ser Val Gly Gly Ser Gly Ile Phe Leu Glu Thr Ser
1               5                   10                  15

Gly Gly Lys Glu Ser Arg Ala Lys Lys Phe Gln Arg Gln His
            20                  25                  30

<210> SEQ ID NO 45
<211> LENGTH: 28
<212> TYPE: PRT
<213> ORGANISM: Artificial Sequence
```

<220> FEATURE:
<223> OTHER INFORMATION: Synthetic polypeptide

<400> SEQUENCE: 45

His Gly Asp Ala Ser Val Gly Ser Gly Ile Phe Leu Glu Thr Ser Gly
1               5                   10                  15

Lys Glu Ser Arg Ala Lys Lys Phe Gln Arg Gln His
            20                  25

<210> SEQ ID NO 46
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 46

His Phe Asp Ala Ser Val Ser Gly Ile Phe Leu Glu Thr Ser Lys Glu
1               5                   10                  15

Ser Arg Ala Lys Lys Phe Gln Arg Gln His
            20                  25

<210> SEQ ID NO 47
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 47

His Gly Asp Ala Ser Gly Ile Phe Leu Glu Thr Ser Arg Ala Lys Lys
1               5                   10                  15

Phe Gln Arg Gln His
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 48

His Gly Asp Ala Ser Gly Ile Phe Leu Glu Thr Ser Ala Lys Lys Phe
1               5                   10                  15

Gln Arg Gln His
            20

<210> SEQ ID NO 49
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 49

His Phe Asp Ala Ser Gly Ile Phe Leu Glu Thr Ser Lys Lys Phe Gln
1               5                   10                  15

Arg Gln His

<210> SEQ ID NO 50
<211> LENGTH: 18
<212> TYPE: PRT
<213> ORGANISM: Artificial Sequence

```
<220> FEATURE:
<223> OTHER INFORMATION: Synthetic polypeptide

<400> SEQUENCE: 50

His Gly Asp Ala Ser Gly Ile Phe Leu Glu Thr Ser Lys Phe Gln Arg
1               5                   10                  15

Gln His
```

CIRCULAR STRAINED ZYMOGEN COMPOSITIONS AND METHODS OF USE

RELATED APPLICATION

This application claims the benefit under 35 U.S.C. § 119(e) of U.S. Provisional Application Ser. No. 62/868,841 entitled "CIRCULAR STRAINED ZYMOGEN COMPOSITIONS AND METHODS OF USE" filed on Jun. 28, 2019, the entire contents of which are incorporated by reference herein.

GOVERNMENT SUPPORT

This invention was made with Government support under Grant Nos. R01 GM044783 and R01 CA073808 awarded by the National Institutes of Health (NIH). The Government has certain rights in the invention.

BACKGROUND OF THE INVENTION

Enzymes are molecules that function as biological catalysts to speed up chemical reactions. The majority of enzymes are proteins, but some are catalytic RNA molecules (i.e., ribozymes). Enzymes act upon substrates to make a product, but, like catalysts, are not consumed by the reaction. Enzymes also tend to be specific for substrates, making them ideal candidates for targeted treatments.

Proteases are a type of enzyme that can break down proteins and peptides by hydrolysis of peptide bonds in a process known as protein catabolism. Proteases typically act on (i.e., cleave) a substrate at a specific proteolytic sequence. This specificity can be used for therapeutic purposes—e.g., targeted cytotoxicity. One example of such a protease is HIV-1 protease, an enzyme that is essential for the life-cycle of HIV.

The treatment of HIV remains a fundamental medical challenge. Numerous antiviral compounds that target many aspects of the viral lifecycle have achieved clinical utility. These antiviral compounds can suppress a patient's viral load to below detectable limits, but treatment must continue as viremia rebounds upon suspension of therapy. While these treatments have transformed HIV from a death sentence to a chronic illness, a cure remains elusive.

A key challenge in the treatment of AIDS is latency of the virus. Early in HIV infection, a subset of CD4+ cells become infected with the virus and then undergo quiescence thereby harboring the integrated HIV provirus without producing viral RNA or proteins. An emerging eradication approach is stimulation of virus production to induce cytopathic effects, but activation alone is proving insufficient to kill latently infected cells. Recent strategies to target cells that produce viral proteins with cytotoxic chemotherapeutic agents are a missing piece of eradication approaches.

SUMMARY OF THE INVENTION

The present disclosure is based, at least in part, on the discovery and identification of circular strained zymogens of RNase 1 that are activated upon cleavage by a specific protease. These zymogens are characterized by imposed strain, a significant level of catalytic inactivation relative to their parent enzyme (i.e., the enzyme from which they derived), a significant recovery of catalytic activity following their protease-mediated activation, and thermal stability.

Accordingly, one aspect of the present disclosure provides a circular zymogen of ribonuclease 1 (RNase 1) having (i) a truncated C-terminus and (ii) either a wild-type N-terminus or a truncated N-terminus that are connected by a bridge that comprises a proteolytic cleavage site, wherein the truncated C-terminus has at least 4 residues truncated and the truncated N-terminus has 1 to 6 residues truncated. In some embodiments, the circular zymogen of RNase 1 is activated by cleavage of the proteolytic cleavage site by a specific protease. In some embodiments, the specific protease is a pathogen-specific protease.

In some embodiments, the specific protease is a disorder-specific protease. In some embodiments, the specific protease is HIV-1 protease. In some embodiments, the total number of residues truncated from the C-terminus and the N-terminus is greater than the total number of residues in the bridge. In some embodiments, the zymogen has a truncated N-terminus, and the truncated C-terminus has 6 residues truncated and the truncated N-terminus has 3 to 6 residues truncated.

Another aspect of the present disclosure provides a circular zymogen of RNase 1 having (i) a truncated C-terminus and (ii) either a wild-type N-terminus or a truncated N-terminus that are connected by a bridge that comprises a proteolytic cleavage site, wherein the circular zymogen is inactivated greater than $10^4$-fold relative to the catalytic activity of wild-type RNase 1.

Another aspect of the present disclosure provides a circular zymogen of RNase 1 having (i) a truncated C-terminus and (ii) either a wild-type N-terminus or a truncated N-terminus that are connected by a bridge that comprises a proteolytic cleavage site, wherein the circular zymogen of RNase 1 is activated by cleavage of the proteolytic cleavage site by a specific protease resulting in a catalytic activity less than 2-fold less than the catalytic activity of wild type RNase 1.

Another aspect of the present disclosure provides a circular zymogen of RNase 1 having native termini that are connected by a bridge that comprises a proteolytic cleavage site and has less than 12 residues. In some embodiments, the circular zymogen of RNase 1 is activated by cleavage of the proteolytic cleavage site by a specific protease. In some embodiments, the bridge has 8 residues.

Another aspect of the present disclosure provides a circular zymogen of ribonuclease 1 (RNase 1) having a His119 residue, wherein an alpha carbon on the His119 residue is displaced by greater than 1 Å relative to His119 in wild-type RNase 1.

Another aspect of the present disclosure provides a circular zymogen of ribonuclease 1 (RNase 1) having a His12 residue, wherein an alpha carbon on the His12 residue is displaced by greater than 1 Å relative to His12 in wild-type RNase 1.

Another aspect of the present disclosure provides a circular zymogen of ribonuclease 1 (RNase 1) comprising an amino acid sequence of His12-X-P-X'-His119,
wherein His12 is a histidine-12 residue,
X is a sequences of 1 or more amino acid residues,
X' is a sequence of 1 or more amino acid residues,
P is a proteolytic cleavage site,
His119 is a histidine-119 residue,
and the number of residues in His12-X-P-X'-His119 is less than 30 residues.
In some embodiments, the circular zymogen is characterized as having strain that is increased by reducing the number of residues in the His12-X-P-X'-His119 amino acid sequence, reducing the number of residues between His12 and P, or reducing the number of residues between His 119 and P.

In some embodiments, the present disclosure provides a composition having a circular zymogen as contemplated herein. In some embodiments, the present disclosure provides a pharmaceutical composition having a circular zymogen as contemplated herein.

Another aspect of the present disclosure provides a method of treating a subject, comprising administering to a subject having a disorder characterized by a specific protease, an effective amount of a circular zymogen as contemplated herein, wherein the proteolytic cleavage site is cleaved by the specific protease. In some embodiments, the disorder is an infection and the specific protease is a pathogen specific protease. In some embodiments, the disorder is AIDS/HIV infection and the specific protease is HIV-1 protease.

These and other aspects and embodiments of the invention are set forth in greater detail herein.

BRIEF DESCRIPTION OF THE DRAWINGS

The following drawings form part of the present specification and are included to further describe certain aspects of the present disclosure. It is to be understood that the data illustrated in the drawings in no way limit the scope of the disclosure. Color versions of the drawings can be found in the USPTO file wrapper of the priority application.

In the drawings.

Wild-type values are as indicated in the present disclosure. Errors bars correspond to standard deviation, with the exception of Str zymogen stabilities where they correspond to standard error.

Figure 4:
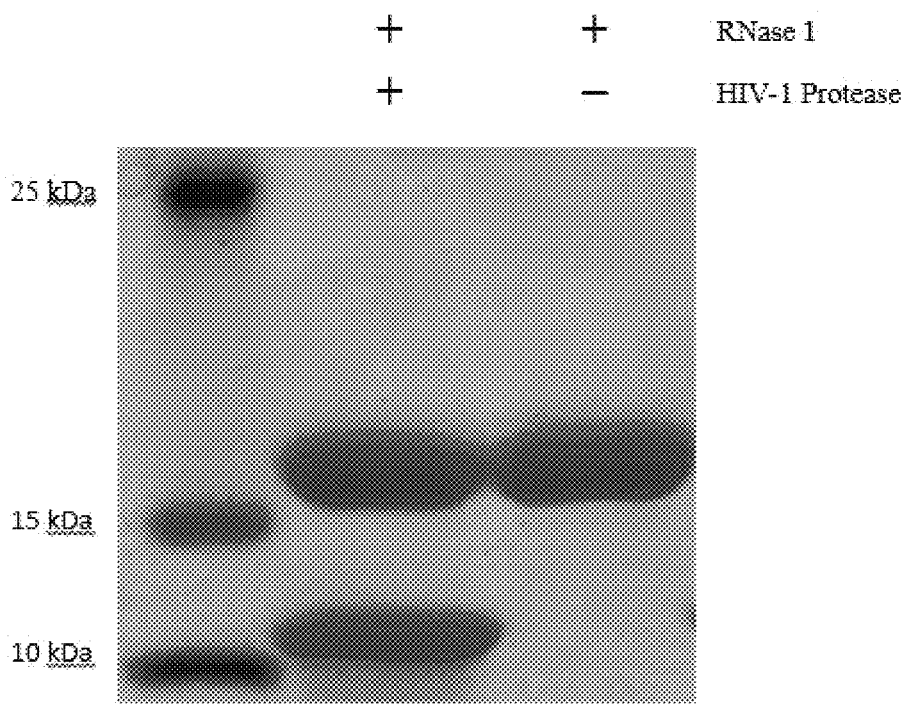

FIG. 4 shows the proteolytic treatment of RNase 1 with HIV-1 protease. After 3 hours of treatment at 37° C., no detectable cleavage of wild-type RNase 1 was observed.

Figure 5:
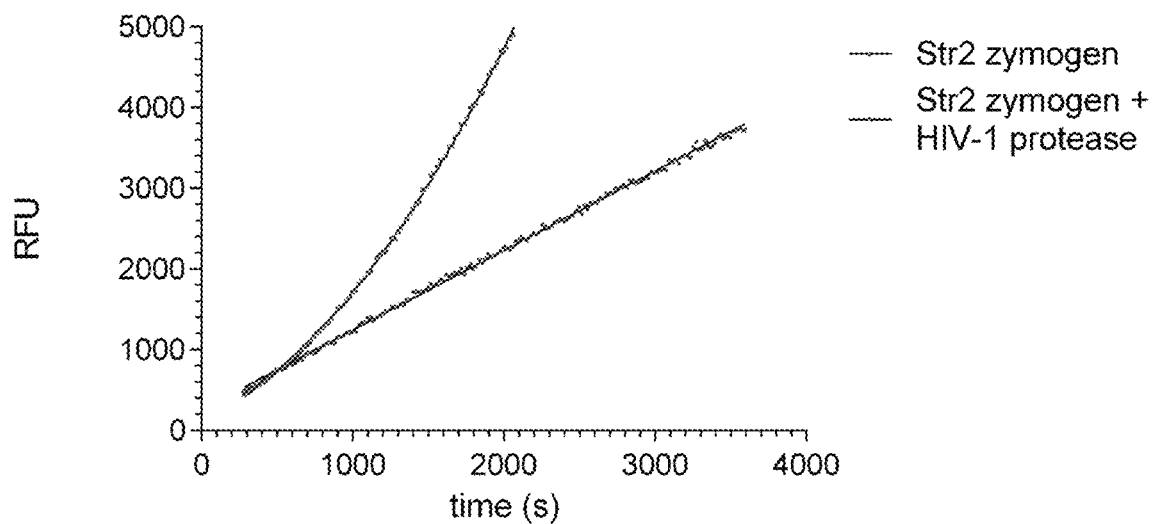

FIG. 5 shows the activation kinetics of Str2. Hydrolysis of 20 nM of fluorogenic RNase substrate at pH 5.0 by 10 nM Str2 zymogen lead to a linear increase in product formation (as reported by RFU) at substrate turnover below 10%. Addition of 2.6 nM HIV-1 protease leads to a time dependent increase in activity, which is fit by a second-order polynomial.

Figure 6A:
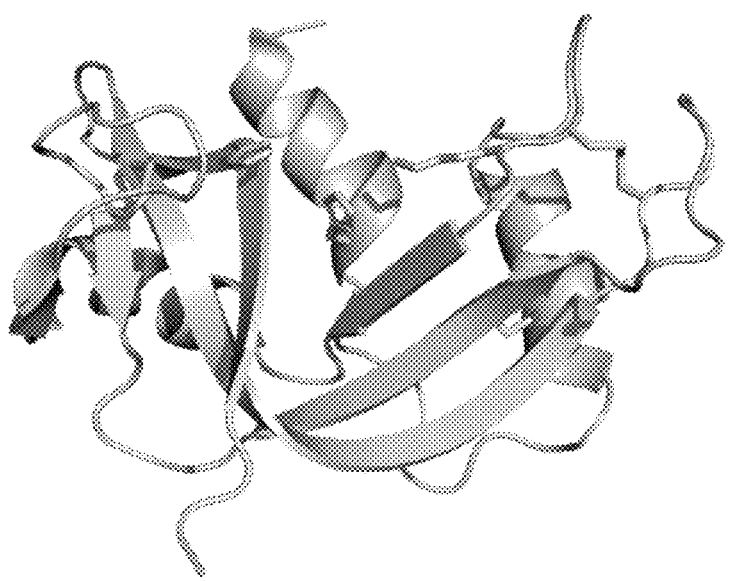
Figure 6B:
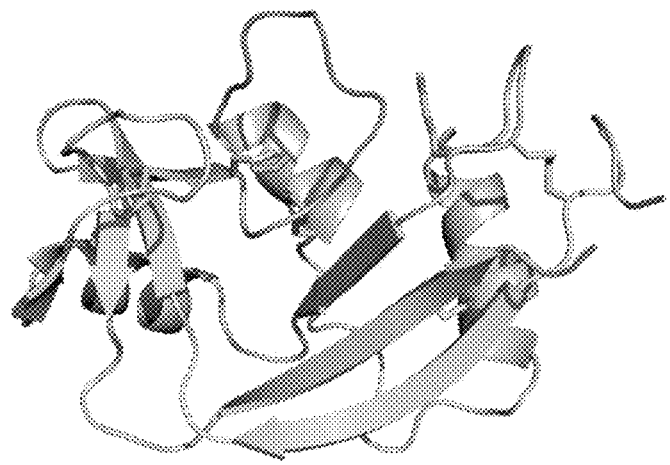
Figure 6C:
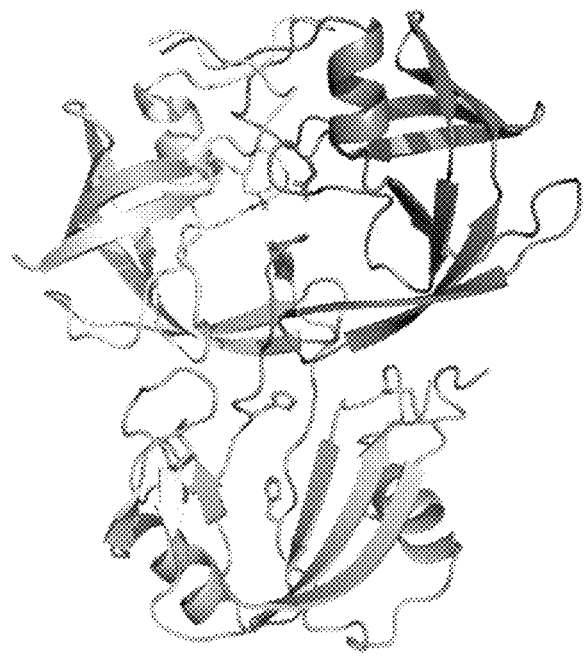

FIGS. 6A-C show the modelling of Str2 zymogen and complex with HIV-1 protease. The active site residues H12, K41, and H118 and disulfide-bonded cysteine sidechains are shown as sticks. FIG. 6A: Connecting the termini of wild-type RNase 1 with a flexible linker and truncating 4 residues from the N-terminus and 6 residues from the C-terminus prevents both terminal secondary structure elements from folding. FIG. 6B: The lowest energy structures generated by Rosetta are predicted to have an unfolded C-terminal β-strand. FIG. 6C: Unfolding of both terminal secondary structural elements are required for HIV-1 protease to recognize the substrate containing linker as modelled by Rosetta.

Figure 7A:
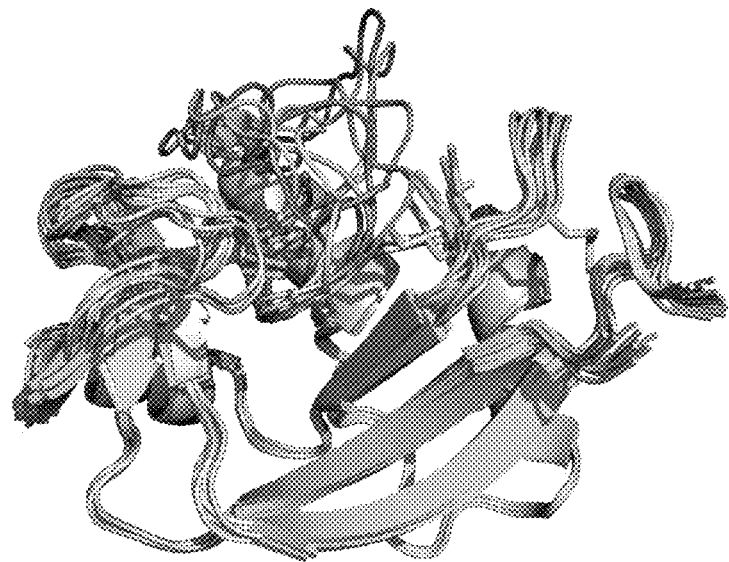
Figure 7B:
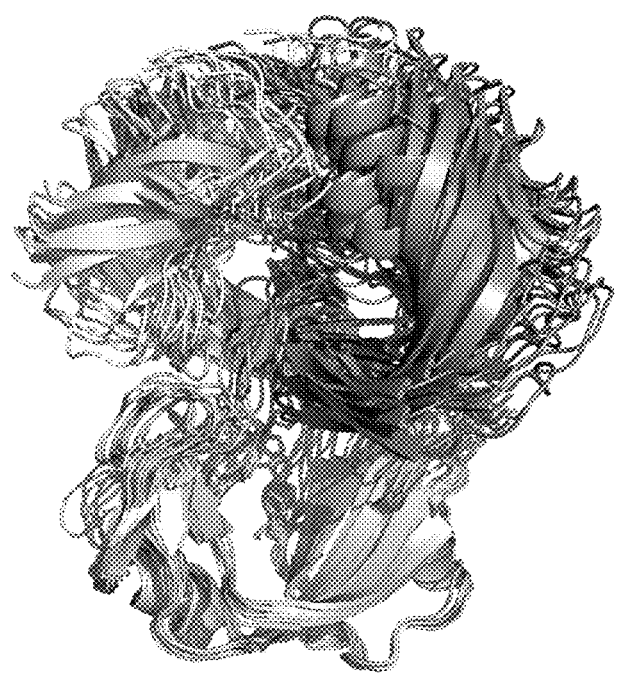

FIGS. 7A-B show the top-10 scoring Rosetta models of Str2 and complex with HIV-1 protease. FIG. 7A: The linker-inactivated zymogen is predicted to occupy multiple conformations which indicates this region may be conformationally dynamic. FIG. 7B: HIV-1 protease requires partial unfolding of RNase 1 in order to close its flaps on the substrate-containing linker.

Figure 8:
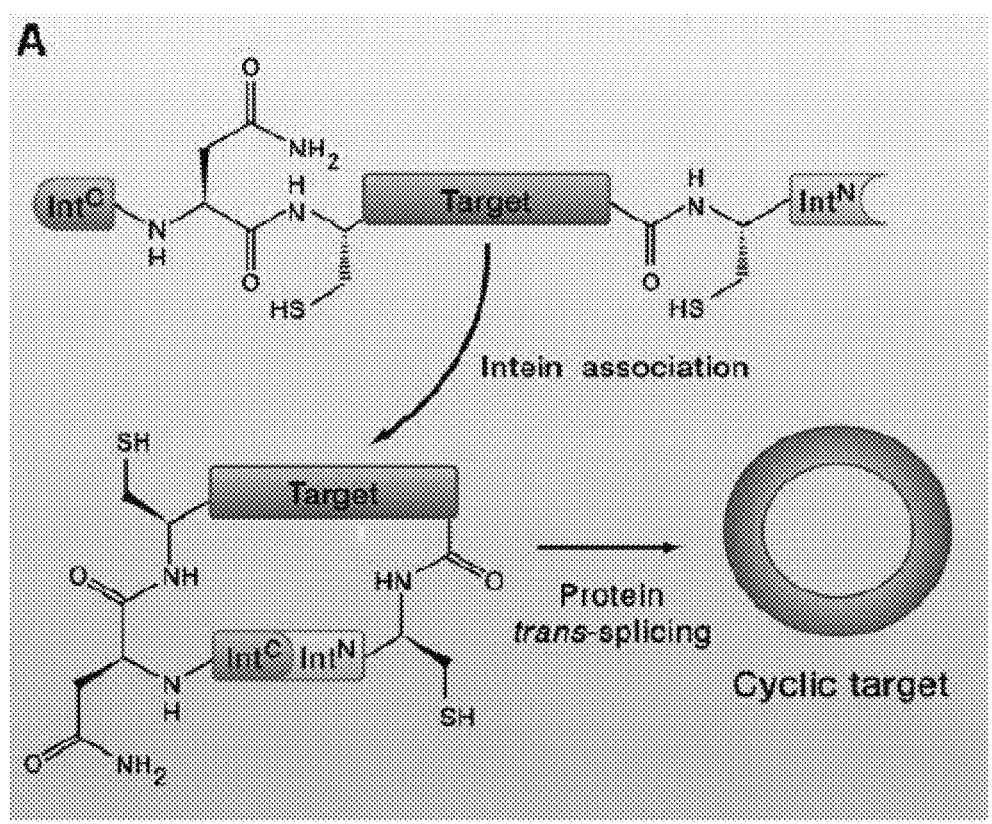

FIG. 8 includes a schematic, from Vila-Perelló, M., & Muir, T. W. (2010). Cell, 143(2), 191-200, showing an example of intein-mediated cyclization. See.

DETAILED DESCRIPTION OF THE INVENTION

The present disclosure provides circular, strained zymogens of RNase 1 that are activated upon cleavage by a specific protease (e.g., HIV-1 protease). These zymogens may be used in the treatment of infections or disorders that are characterized by the presence of a specific proteolytic enzyme (or protease, as the terms are used interchangeably herein). Such proteolytic enzyme is solely or predominantly present in a particular pathogen or pathogen-infected cells or in diseased cells and therefore the activity of the zymogen after its activation, which may include cytotoxicity, is limited to those specific pathogens or cells. As an example, a zymogen that is activated by HIV-1 protease would target HIV-positive cells, preferably killing or weakening such cells. The zymogens therefore enable targeted cytotoxicity.

The zymogens of this disclosure are designed to be cleaved and thereby activated by a specific protease that is found only or predominantly in a pathogen or cells infected by the pathogen or in otherwise diseased cells of a subject. The zymogens exhibit high levels of catalytic inactivation (e.g., >10,000 fold and in some cases up to 28,000 fold relative to wild-type RNase 1, their parent enzyme). The zymogens also exhibit high stability (e.g., thermostability). The catalytic inactivation and thermostability of the zymogens of the present invention are greater than those of non-circular zymogens and non-strain zymogens previously described.

Zymogen

A zymogen (or proenzyme as the terms are used interchangeably herein) is a variant of a wild-type or parent enzyme, and has reduced, and in some instances negligible, enzymatic activity relative to the wild-type or parent enzyme. Zymogens can be converted to an active enzyme, thereby recovering some of the activity of their wild-type counterpart. The zymogens of this disclosure are activated by a protease (i.e., by proteolytic cleavage or by protease-mediated cleavage). Such activation may be referred to as protease-mediated (zymogen) activation. An activating protease cleaves the zymogen of this disclosure, thereby increasing its catalytic activity including for example restoring the catalytic activity to wild-type levels.

Enzymes that can be cytotoxic or cause damage ex situ (e.g., proteases) are ideal zymogen candidates. For example, proteases involved in blood coagulation and digestion and apoptotic caspases have been used in a zymogen form. The endogenous production of such an enzyme (e.g., a cytotoxic protein) requires precise regulation and often includes safeguards to attenuate enzymatic activity until the zymogen arrives at the intended location. The zymogens then can be activated by proteolytic activity. In some instances, the zymogen has no measurable enzymatic activity. In some instances, the zymogen has about 1, 2, 3, 4, 5, 6, 7, 8, 9, 10, 11, 12, 13, 14, 15, 16, 17, 18, 19, or 20-fold less enzymatic activity than its wild-type or parent enzyme. In some instances, a zymogen has more than 20-fold less enzymatic activity than the wild-type enzyme. In some instances, the zymogen has about 50, 100, 250, 500, 750, 1000, 2000, 3000, 4000, 5000, 6000, 7000, 8000, 9000, or 10000 fold less enzymatic activity than its wild-type or parent enzyme. In some instances, the zymogen has about 20,000 or 30,000 fold less enzymatic activity than its wild-type or parent enzyme. In some instances, the zymogen has about 28,000 fold less enzymatic activity than its wild-type or parent enzyme.

RNase 1

The present disclosure provides, in part, circular strained zymogens of RNase 1. RNase 1 (also referred to as human pancreatic ribonuclease, HP-RNase, EC 3.1.27.5, or Uni-ProtKB P07998) is a pancreatic-type ribonuclease. Ribonucleases are enzymes that degrade RNA. Ribonucleases have the ability to form a complex with single-stranded RNA; the complex arises by an extended multi-site cation-anion interaction between lysine and arginine residues of the enzyme and phosphate groups of the RNA. Ribonucleases are a privileged suitable class of enzymes for the creation of zymogens due to their therapeutically desirable properties: cell permeability and cytotoxic activity.[24]

RNase 1 is an endoribonuclease that preferentially hydrolyzes single-stranded RNA to nucleoside 3'-monophosphates via nucleoside 2',3'-cyclic monophosphate intermediates. RNase 1 protein is monomeric and preferentially degrades single-stranded RNA over double-stranded RNA. An exemplary amino acid sequence for wild-type RNase 1 is shown below:

```
                                              (SEQ ID NO: 2)
    KESRAKKFQR QHMDSDSSPS SSSTYCNQMM RRRNMTQGRC

KPVNTFVHEP LVDVQMVCFQ EKVTCKNGQG NCYKSNSSMH

ITDCRLTNGS RYPNCAYRTS PKERHIIVAC EGSPYVPVHF

DASVEDST
```

All the zymogens of the present disclosure are described based on the sequence above.

The foregoing sequence corresponds to the mature RNase 1 protein, and lacks the signal sequence for secretion from human cells which may be present in less mature forms of the protein. The mature protein is 128 amino acids in length, while the less mature form may be 156 amino acids in length due to the presence of 28 amino acids at the n-terminus of the mature protein.

Circular Zymogens of RNase 1

The current disclosure provides what is believed to be the first known circular zymogen of RNase 1. The zymogens provided herein include a bridge that connects the amino (N) terminus to the carboxyl (C) terminus. Without being bound by theory or mechanism, the bridge blocks the active site, thereby interfering and in some instances preventing substrate binding.

The circular strained zymogens may be created using circular permutation, which links the native N-terminus of RNase 1 to the native C-terminus of RNase 1 via the bridge. As used herein, the terms "bridge" and "linker" are used interchangeably. The bridge may be comprised of amino acids (also referred to as residues).

Circular permutation is a process by which the order of amino acids in a protein may be changed, typically as a result of a change in the amino and carboxy termini, but in most cases without a significant change to the overall 3-dimensional (3D) structure of the protein. Circular permutations occur in nature due to evolutionary events or posttranslational modifications. Circular permutations can also be artificially engineered, as in the present case. Circular permutation also involves the creation of new termini at different locations within the amino acid sequence of the protein. The potential sites for the new termini are dependent on the type of protein, and are usually selected based on which new termini sites will be less disruptive to the 3-dimensional conformation of the protein. In some embodiments, for the RNase 1 zymogens of the present disclosure, the new termini are created at the 88/89 positions.

Circular permutation typically creates a zymogen with open (or free) termini, which is an intermediate structure in the process of making the circular zymogens of the present disclosure. The RNase 1 zymogens made by circular permutation according to this disclosure may be converted into circular (contiguous) zymogens through the use of intein-mediated cyclization (also referred to as intein-mediated cis-splicing). An intein (also referred to as a protein intron) is a segment of a protein that is able to excise itself and ligate (join) the remaining portions (the exteins) with a peptide bond in a process termed protein splicing. During intein-mediated cyclization of the zymogen intermediates, an intein is placed on the newly created N- and C-termini of the intermediate. Thereafter, the inteins catalyze a multistep posttranslational protein modification through which the intein is excised and the ends that previously flanked the intein are ligated to form a contiguous peptide (contiguous zymogen), joined by one sequence. The resultant zymogen is a circular zymogen because it has no open (or free) termini. An illustration of the process of intein-mediated cyclization is shown in FIG. 8 and taken from Vila-Perelló, M., & Muir, T. W. (2010). Cell, 143(2), 191-200. Further reference may be made to Vila-Perelló et al. for a more detailed discussion of intein-mediated cis-splicing.

Truncation

The zymogens of this disclosure may be shorter in length than their parent protein. This is accomplished by truncating the sequence of the parent protein at one or both of its native amino and carboxy termini. As used herein, the term "truncation" refers to the removal of amino acids from a wild-type terminus of a parent protein (e.g., RNase 1). Methods for truncating amino acids are known in the art. A terminus with 1 or more residues removed is referred to as a "truncated terminus". In some embodiments, the zymogens have a truncated N-terminus relative to their parent proteins (and the zymogen is referred to as being N-truncated). In some embodiments, the zymogens have a truncated C-terminus relative to their parent protein (and the zymogen is referred to as being C-truncated). In some embodiments, both the N- and C-terminus are truncated relative to the parent protein. The degree of truncation may be expressed by the absolute number of amino acids removed from the amino terminus, or the carboxy terminus, or both the amino and carboxy termini, or it may be expressed as a % of the amino acids removed relative to the full length of the parent protein.

In some embodiments, the N-terminus of the zymogen is not truncated relative to the parent protein and thus it has a wild-type N-terminus (also referred to as native N-terminus). In some embodiments, the C-terminus of the zymogen is not truncated relative to the parent protein and thus it has a wild-type C-terminus (also referred to as native C-terminus). In RNase 1, the wild-type N- and C-termini are at amino acid K (lysine) (position 1) and amino acid T (threonine) (position 128), respectively. In some embodiments, both the N- and C-termini are wild-type termini.

In some embodiments, the RNase 1 zymogen has its first terminal amino acid truncated from the N-terminus (i.e., lysine at position 1). N-truncation may remove 1, 2, 3, 4, 5, 6, 7, or more amino acids from the N-terminus. In some embodiments, truncation at the N-terminus removes any one of the following amino acid sequences, with K being in position 1 of the N-terminus: K, KE, KES, KESR (SEQ ID NO: 3), KESRA (SEQ ID NO: 4) and KESRAK (SEQ ID NO: 5).

In some embodiments, the RNase 1 zymogen has its first terminal amino acid truncated from the C-terminus (i.e., threonine at position 128). C-truncation may remove 1, 2, 3, 4, 5, 6, 7, or more amino acids from the C-terminus. In some embodiments, truncation at the C-terminus removes any one of the following amino acid sequence with T being in position 128 (i.e., the last amino acid in the protein): T, ST, DST, EDST (SEQ ID NO: 6), VEDST (SEQ ID NO: 7), and SVEDST (SEQ ID NO: 8).

A circular RNase zymogen provided herein can have any combination of the above mentioned degrees of N- and C-truncation. In some embodiments, the N-, C- or both the N- and C-termini are truncated. In some instances, the amino acid sequence of RNase 1 comprising position 7 through to position 122 is retained in the zymogen.

Bridge

Circular zymogens of the present disclosure include a bridge that spans the native termini without distorting protein structure. In some instances, the new termini may introduce some distortion (or disruption) of the 3D structure.

Installing a bridge of insufficient length to permit folding of both the N- and C-terminal secondary structural elements imposes strain on the active site and inactivates RNase 1 zymogens. In some embodiments, the catalytic inactivation is up to 28,000-fold. Disulfide bonds limit distortion of the fold to the termini allowing these zymogens to maintain conformational stability above physiological temperature. Though a moderate reduction in efficiency is observed, the strained zymogens are still readily cleaved by HIV-1 protease, which restores wild-type ribonucleolytic activity.

In some instances, the bridge links the wild-type termini (or native termini) to each other. In some instances, the bridge links a native N-terminus to a truncated C terminus. Alternatively, the bridge can link a truncated N-terminus to a native C-terminus. The bridge can link the termini of a zymogen having any degree of truncation or combination of N- and C-truncation as described herein. In some embodiments, the bridge is 14 residues in length. In some embodiments, the bridge is less than 14 residues in length. In some embodiments, the bridge is 13, 12, 11, 10, 9, 8, 7, 6, 5, 4, 3, 2 or 1 residue(s) long. The bridge may have a length in the range of 1-14 residues, 1-13 residues, 1-12 residues, 1-11 residues, 1-10 residues, 1-9 residues, 1-8 residues, 1-7 residues, 1-6 residues, 1-5 residues, or 1-4 residues.

The bridge is typically comprised of amino acids.

Proteolytic Cleavage Site

The bridge comprises the proteolytic cleavage site. As used herein, a proteolytic cleavage site is an amino acid sequence that is cleaved by a protease. Typically, the proteolytic cleavage site of the protease is specific for the protease. In some embodiments, the protease is pathogen-specific. For example, in some embodiments, the protease is specific to a pathogen (e.g., HIV), such that it is found only or predominantly in cells infected with the pathogen. In some embodiments, the protease is disorder-specific. For example, in some embodiments, the protease is specific to a particular disorder, such that it is found only or predominantly in cells that are in the diseased state. In some embodiments, the protease is expressed in pathogen-infected or diseased cells at a higher level than in normal, non-infected, non-diseased cells (e.g., 0.5, 1, 2, 3, 4, 5, 6, 7, 8, 9, 10, or more fold greater expression than in such normal cells).

In some instances, the bridge comprises a proteolytic cleavage site and one or more additional residues on the N-terminus and/or the C-terminus of the proteolytic cleavage site. These residues are referred to herein as flanking residues. In some instances, the bridge comprises a proteolytic cleavage site and one or more flanking residues on the N-terminus of the proteolytic cleavage site. In some instances, the bridge comprises a proteolytic cleavage site and one or more flanking residues on the C-terminus of the proteolytic cleavage site. There may be 1, 2, 3, 4, 5, 6, 7, 8, 9, 10 or more flanking residues. In instances when the proteolytic cleavage site is flanked by one or more residues, the number of flanking residues on the N-terminus of the proteolytic cleavage site may be the same as the number of flanking residues on the C-terminus of the proteolytic cleavage site. Alternatively, the number of flanking residues on the N-terminus of the proteolytic cleavage site may be different from the number of flanking residues on the C-terminus of the proteolytic cleavage site. The flanking residues in the bridge, other than the proteolytic cleavage site residues, can be any amino acid or any amino acid sequence. In some instances, the flanking residues include at least one glycine residue. In some instances, the flanking residues are all glycine residues. In some embodiments, the total number of residues in the bridge, including flanking residues and proteolytic cleavage site residues, is greater than the total number of truncated residues (i.e., the sum of residues truncated from the N- and C-termini of the parent protein). In alternative embodiments, the total number of residues in the bridge is less than the total number of truncated residues.

The proteolytic cleavage site may be virtually any proteolytic cleavage site. Non-limiting examples of proteases and proteolytic cleavage sites (and the pathogens or disorders they are associate with) that can be used in the circular zymogens are known in the art and are reproduced in Table 1. In some embodiments, the protease may be any protease associated with the disorders in Table 1. The cleavage site is illustrated with a downwards-facing arrow to indicate the location of cleavage. For example, the KPIEF↓LELK sequence (SEQ ID NO: 9) is cleaved at the location of the arrow, thus cleaving sequences KPIEF (SEQ ID NO: 10) from LELK (SEQ ID NO: 11). Similarly, cleavage site having SEQ ID NO: 12 is shown along with the its cleavage products represented by SEQ ID NOs: 13 and 14. In similar fashion, it will be understood that cleavage sites represented by SEQ ID NO: 1 and 15-22 will give rise to cleavage products that comprise sequences on either side of the downwards-facing arrow.

TABLE 1

| Zymogen Targets | | |
|---|---|---|
| Disease | Protease | Cleavage Site and/or Products |
| Malaria | plasmepsin II | KPIEF↓LELK (SEQ ID NO: 9)<br>KPIEF (SEQ ID NO: 10)<br>LELK (SEQ ID NO: 11) |

TABLE 1-continued Zymogen Targets

| Disease | Protease | Cleavage Site and/or Products |
|---|---|---|
| HIV/AIDS | HIV-1 | SGIF↓LETS (SEQ ID NO: 1)<br>TATIM↓MQRGN (SEQ ID NO: 12)<br>TATIM (SEQ ID NO: 13)<br>MQRGN (SEQ ID NO: 14) |
| Hepatitis C Infection | NS3 | EDVVCC↓SMSY (SEQ ID NO: 15)<br>EDVVAC↓SMSY (SEQ ID NO: 16) |
| SARS-CoV Infection | 3CL$^{pro}$ | AVLQ↓SGFR (SEQ ID NO: 17) |
| SARS-CoV-2 Infection | 3CL$^{pro}$ | AVLQ↓SGFR (SEQ ID NO: 18)<br>ATLQ↓SGNA (SEQ ID NO: 19) |
| Cancer | MMP-2 | PLG↓AG (SEQ ID NO: 20) |
| Cancer | MMP-9 | IPVS↓RSG (SEQ ID NO: 21) |
| Leukemia | HTLV-1 | PPVIL↓PIQA (SEQ ID NO: 22) |

If a circular zymogen is intended for therapeutic purposes, preferably its proteolytic cleavage site is not also a cleavage site for an endogenous human protease. Such common usage of the cleavage site between the zymogen and the endogenous human protease can be discerned and, thereby, avoided by performing experiments in which a circular zymogen is incubated with, for example, human serum or extracts from human cells. Cleavage can then be detected by SDS-PAGE or by assays of ribonucleolytic activity. Useful information can also be obtained from on-line databases. For example, the MEROPS database can be used to identify human proteases that cleave a particular sequence of amino acids (see ebi.ac.uk/merops/cgi-bin/specsearch.pl website). The Reactome database (see reactome.org website) and Human Protein Atlas database (see proteinatlas.org website) can be used to identify tissues that harbor human proteases as well as the localization of the protease (e.g., extracellular, cytosolic, lysosomal, etc.). This information on substrate specificity and location can provide guidance in the choice of a proteolytic cleavage site for a circular zymogen that is intended to treat a particular disease.

Non-limiting examples of circular zymogen designs that can be made using an HIV-1 proteolytic cleavage site (e.g., SGIFLETS; SEQ ID NO: 1) are provided in Table 2.

TABLE 2

G and Str Zymogen Designs

| Zymogen | Linker | N-truncation | C-truncation |
|---|---|---|---|
| 3G | GGGSGIFLETSGGG (SEQ ID NO: 23) | None | EDST (SEQ ID NO: 6) |
| 2G | GGSGIFLETSGG (SEQ ID NO: 24) | None | EDST (SEQ ID NO: 6) |
| 1G | GSGIFLETSG (SEQ ID NO: 25) | None | EDST (SEQ ID NO: 6) |
| 0G | SGIFLETS (SEQ ID NO: 1) | None | EDST (SEQ ID NO: 6) |
| Str1 | SGIFLETS (SEQ ID NO: 1) | KES | SVEDST (SEQ ID NO: 8) |
| Str2 | SGIFLETS (SEQ ID NO: 1) | KESR (SEQ ID NO: 3) | SVEDST (SEQ ID NO: 8) |
| Str3 | SGIFLETS (SEQ ID NO: 1) | KESRA (SEQ ID NO: 4) | SVEDST (SEQ ID NO: 8) |
| Str4 | SGIFLETS (SEQ ID NO: 1) | KESRAK (SEQ ID NO: 5) | SVEDST (SEQ ID NO: 8) |

In some embodiments, the proteolytic cleavage site is a substrate for HIV-1 protease (e.g., SGIFLETS (SEQ ID NO: 1)). Non-limiting examples of substrates that can be used in the zymogens of the present disclosure are provided in Table 3.

TABLE 3

Examples of substrates for HIV-1 protease (Beck et al. (2000) Virology 274, 391-401). Peptide sequence/cleavage site

1) GSGIF LETSL (SEQ ID NO: 26)

2) GSGVF VETSL (SEQ ID NO: 27)

3) SGGSGVY HVSTLVPEF (SEQ ID NO: 28)

4) GSGVF VEMPL (SEQ ID NO: 29)

5) SGGSGVF VVNGLVPEF (SEQ ID NO: 30)

6) GSGNY LVTSL (SEQ ID NO: 31)

7) GSGVY LATDL (SEQ ID NO: 32)

8) SGGSGIM FESNLVPEF (SEQ ID NO: 33)

9) GSGIM FQSAL (SEQ ID NO: 34)

10) GSGNY FVQGL (SEQ ID NO: 35)

11) GSGNY FVETL (SEQ ID NO: 36)

12) IRKIL FLDG (SEQ ID NO: 37)

13) VSQNY PIVQN (SEQ ID NO: 38)

14) GSGLF TEYGL (SEQ ID NO: 39)

Enzymatic Activity

The zymogens of this disclosure have a reduced enzymatic activity relative to their parent proteins. As used herein, the terms "enzymatic activity", "catalytic activity", and "catalytic efficiency" are used interchangeably and refer to the ability of the zymogen or enzyme to cleave or digest its substrate. Without limitation, two methods that can be used to measure enzyme activity are: (i) to measure the decrease in substrate concentration in a period of time, and (ii) to measure the increase in concentration of a product after a period of time.

Ideally, a zymogen exhibits high degrees of catalytic inactivation. As used herein, "catalytic inactivation" refers to the degree to which catalytic activity has been reduced in the zymogen relative to its wild-type enzyme (e.g., RNase 1).

As used herein, the term "proteolytic activation" refers to the process by which the zymogen is converted to an active enzyme via proteolytic cleavage. The catalytic activity of a zymogen has been partially or completely restored relative following activation, including protease-mediated activation. As used herein, the term "activated zymogen" refers to the enzyme produced upon proteolytic cleavage of the zymogen, as described herein. The circular zymogens of the present disclosure are activated by the action of a protease. They are not activated by a chemical reagent (e.g., 2-nitro-5-thiocyanatobenzoic acid). The catalytic activity of wild-type RNase 1 is $2.1\pm0.2\times10^7$ $M^{-1}s^{-1}$ (Johnson et al. Biochemistry 2007, 46 (36), 10308-10316, the relevant disclosures of which are herein incorporated by reference for the purpose and subject matter referenced herein).

Unexpectedly, it was found that the circular RNase 1 zymogens of the present disclosure exhibit over 10,000-fold catalytic inactivation (i.e., the catalytic activity of these zymogens is <0.01% of the catalytic activity of their parent protein RNase 1). This degree of inactivation is significantly greater than the catalytic inactivation observed for previous zymogens (e.g. the circularly permuted RNase zymogens in U.S. Pat. No. 7,098,016, the relevant disclosures of which are herein incorporated by reference for the purpose and subject matter referenced herein). In some embodiments, the catalytic inactivation relative to wild-type activity is greater than 2-fold (e.g., 3, 4, 5, 6, 7, 8, 9, 10, 11, 12, 13, 14, 15, 16, 17, 18, 19, or 20-fold). In some embodiments, the catalytic inactivation is about 10000, 10500, 11000, 11500, 12000, 12500, 13000, 13500, 14000, 14500, 15000, 15500, 16000, 16500, 17000, 17500, 18000, 18500, 19000, 19500, 20000, 20500, 21000, 21500, 22000, 22500, 23000, 23500, 24000, 24500, 25000, 25500, 26000, 26500, 27000, 27500, 28000, 28500, 29000, 29500, or 30000-fold relative to wild-type activity. In some embodiments, the catalytic inactivation is any range of numbers therein. In some embodiments, the catalytic inactivation is up to 28,000-fold.

Unexpectedly, it was also found that the circular RNase 1 zymogens of the present disclosure reach near-wild-type levels of catalytic activity after activation-closer to wild-type levels than previous zymogens. In some embodiments, the catalytic activity of the activated zymogen is less than 2-fold less than the catalytic activity of wild type RNase 1. In some embodiments, the catalytic activity of the activated zymogen is less than 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0-fold less than the catalytic activity of wild-type RNase 1.

Thermal Stability

Additionally, the zymogens of the present disclosure exhibit improved thermal stability relative to previously described zymogen designs (e.g., non-circular zymogen designs). An additional advantage of the zymogens of the present disclosure is that, with progressive truncation (i.e., increasing truncation), they exhibit a disproportionately greater reduction in enzymatic activity relative to the corresponding reduction in thermal stability. In other words, the more truncated they are, the more catalytically inactive they are without significant loss of thermal stability. Thermal stability can be improved by introducing artificial disulfide bonds into the zymogen. A zymogen having "improved thermal stability" may be defined as a zymogen having a melting temperature, or a temperature at the midpoint of the thermal transition between folded and unfolded states ($T_m$), that is at least 10° C. above physiological temperatures. "Physiological temperature" refers to the normal body temperature for a subject. Human physiological temperature ranges from 36.5° C.-37.5° C. In some embodiments, "physiological temperature" refers to about 35.0° C., 35.2° C., 35.4° C., 35.6° C., 35.8° C., 36.0° C., 36.2° C., 36.4° C., 36.6° C., 36.8° C., 37.0° C., 37.2° C., 37.4° C., 37.6° C., 37.8° C., or 38.0° C.

In some embodiments, the melting temperature of the zymogens of the present disclosure may be in the range of 35-54° C., 36-54° C., 36-50° C., 36-46° C., 36-40° C., 40-46° C., 40-50° C., and 40-54° C. In some embodiments, the melting temperature is 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C. or any range therein.

Strain

The characteristics of greater catalytic inactivation and greater proteolytic activation relative to previously described zymogens may be due in part to the imposition of strain in the circular zymogens provided herein. Strain may be imposed within the circular zymogen by reducing the number of residues in the bridge or reducing the number of residues between the bridge and the active site. The active site of RNase 1 comprises a pair of residues (His12 and His119) that are important for catalysis and are located near the two native termini.

Figures 1, 2:
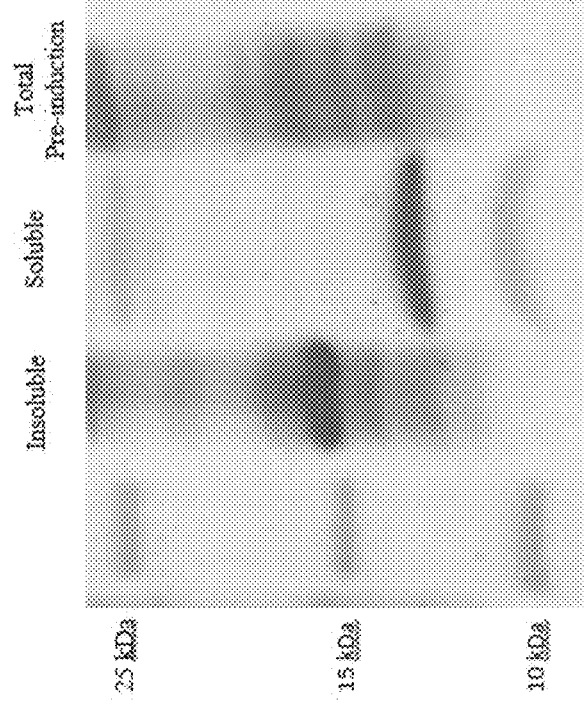
FIG. 1 includes a table showing the number of residues between various zymogen designs with an SGIFLETS (SEQ ID NO: 1) cleavage site targeted by HIV-1 protease. "—" denotes a single peptide bond joining the F and L residues. The Table provides in order SEQ ID NOs: 40-50.
FIG. 2 shows expression of 3G zymogen. Induction of expression of the single open-reading-frame zymogen construct results in a single band in the insoluble fraction (representing the circular zymogen) and two bands in the soluble fraction (representing the intein fragments), neither of which are observed pre-induction, as analyzed by SDS-PAGE.

A difference in the position of His12 in the circular zymogen relative to the position of His12 in the wild-type protein can be used as an indicator of strain. Similarly, a difference in the position of His119 in the circular zymogen relative to the position of His119 in the wild-type protein can be used as an indicator of strain. The positions of His12 or His119 in the zymogen or the wild type protein can be determined relative to each other (e.g., by using superimposed structures, superimposed structures of computer-modelled zymogens and wild type counterparts; comparison of x-ray crystallography images, comparison of computer-modelled zymogens to x-ray crystallography images) or relative to a fixed position in both the zymogen and the wild-type (e.g., an amino acid residue which does not change position between the zymogen and the wild-type protein). In a non-circular zymogen, the termini are not linked and thus these zymogens are not "strained" as the term is used herein. FIG. 1 shows the distance between the two active-site-histidine residues in different zymogen designs. In a linear zymogen, the distance is not applicable because the termini are free (i.e., they are not linked to each other).

Reducing the distance between the His12 or His119 and the proteolytic cleavage site is accomplished by increasing the degree of truncation (on the C-terminus, N-terminus, or both the C- and N-termini). It can also be accomplished by reducing the number residues in the bridge used to link the N and C termini in the circular zymogen. In some instances, strain is increased/introduced in the circular zymogen by introducing a linker that has fewer residues than the number of residues truncated from both of the termini.

Measurement of Strain

Strain in the zymogens can be measured as the displacement of an alpha carbon in an amino acid residue (e.g., His12 or His119). The imposition of strain does not alter the relative orientation of globular domains in a zymogen. The term "strain", as used herein, does not refer to the displacement of globular domains in the zymogen relative to each other. Furthermore, it does not refer to the displacement of globular domains that are distorted. As used, a "globular domain" is a type of protein domain. Protein domains are compact three-dimensional structures that can evolve, function, and exist independently of the rest of the protein chain. They can often be independently stable and folded. They consist of multiple amino acids.

As described in greater detail in the Examples, relocating the termini of RNase 1 during circular permutation moved the His12 and His119 residues and thereby attenuated catalysis while leaving the rest of the protein relatively intact. It was determined empirically that enhanced inactivation was attainable and was accompanied by reduced thermostability, consistent with strain being present in the zymogen.

Computational modelling can be used to measure "strain". For example, models of the str2 zymogen (see Table 2) were prepared using the KIC loop modelling algorithm of the Rosetta computer program (Stein & Kortemme, 2013). A truncated structure of RNase 1 (chain A of pdb 1z7x) with residues 1-7 and 119-124 excised was supplied as the input model. The structure was also permuted at position 88 because Rosetta cannot accommodate circular proteins. The top-10 scoring models were compared to the x-ray crystal structure of RNase 1 (pdb: 1z7x). On average, the alpha carbon of His119 in the str2 zymogen was displaced by >1 Å (1.22 Å for chain A and 1.16 Å for chain C), indicating strain.

A circular zymogen of RNase 1 having an alpha carbon of His12 and/or His119 displaced >1 Å, relative to the position of such amino acid in the wild-type protein, is indicative of strain, and that strain can be measured by the amount of displacement of the alpha carbon in the His 12 and/or His119.

Methods of Use

The zymogens of the present disclosure can be used in vitro and/or in vivo. In vitro, they may be used to modify or manipulate cells such as HIV-infected cells or diseased cells characterized as expressing a particular protease. In vivo, they may be used to treat a subject having an infection or a disorder that is characterized by expression of a protease that is not normally or not highly expressed in non-infected and non-diseased cells in the subject. The protease disclosed herein can be any protease that is specific to a pathogen or a diseased state and is localized to the pathogen, cells infected by the pathogen, or cells that are in the diseased state. The circular zymogen designed with the substrate for said protease in its bridge will be preferentially cleaved in those pathogens or those pathogen-infected cells or in those diseased cells, and such pathogens and cells will be preferentially susceptible to the activity of the activated zymogen, compared to normal non-infected and non-diseased cells. Accordingly, the zymogens may be administered systemically to the subject but their activity is localized to the cells of interest by virtue of being activated only by proteases in such cells.

Non-limiting examples of diseases that can be targeted by the zymogens of this disclosure include malaria, HIV/AIDS, hepatitis C infection, SARS, COVID-19, and cancer such as ovarian cancer and leukemia.

In some embodiments, the zymogens of the present disclosure are used for the treatment of a subject having HIV. In these embodiments, the zymogen comprises a proteolytic cleavage site for HIV-1 protease (e.g., SGIFLETS (SEQ ID NO: 1)). In some embodiments, the zymogen has (i) a truncated C-terminus and (ii) either a wild-type N-terminus or a truncated N-terminus, wherein (i) and (ii) are connected by a bridge that comprises a proteolytic cleavage site (e.g., for HIV-1 protease, such as SGIFLETS (SEQ ID NO: 1)), wherein the truncated C-terminus has at least 4 residues truncated and the truncated N-terminus has 1 or more residues truncated, preferably 3 or more residues truncated.

In some embodiments, the zymogens of the present disclosure are used in a prophylactic manner. In this embodiment, a zymogen is delivered to a subject with the intent of deterring HIV infection. Subjects to be treated prophylactically include the general population, subsets of the population at most risk of developing severe disease (e.g., those with an underlying predisposing condition), those at greatest risk of contact with the pathogen (e.g., essential workers, medical personnel, emergency personnel, etc.), those at greater risk due to age (e.g., the elderly, infants), etc. When used prophylactically, the zymogen may be used at times of greatest risk, including for example seasonally depending on risk (e.g., flu season), within days or hours of engaging in high risk activities such as for example unprotected sexual intercourse, use of non-sterile hypodermic needles, blood transfusion or other tissue transplantation, and the like. When used prophylactically, the zymogen may be administered in amounts effective to prevent the onset of an infection by the pathogen (e.g., prevent occurrence of any symptoms, or prevent pathogen presence in a patient as determined by analysis of a patient sample, etc.) or it may be used in amounts effective to reduce the severity and/or longevity of any such infection (e.g., reduce severity and/or longevity of symptom(s), reduce pathogen load in the patient as determined by analysis of a patient sample, etc.).

The zymogens of the present disclosure may be administered to a subject in the form of a protein. Alternatively, the zymogens may be administered in the form of a nucleic acid construct (e.g., nucleic acid vector) that expresses the zymogen and inteins in order to facilitate the intein-mediated cyclization. In some instances, the vector encodes the zymogen and the flanking inteins.

Suitable techniques for engineering nucleic acid constructs are well known in the art. In some instances, the nucleic acid is RNA. In alternative embodiments, the nucleic acid is DNA. In some embodiments, the nucleic acid is a vector (e.g., a viral vector). A "vector" refers to a nucleic acid capable of transporting another nucleic acid to which it has been linked. The vector may be capable of autonomous replication or integration into the genome of a host cell. Vectors contemplated for use in the present disclosure include, without limitation, those commonly used in genetic engineering technology, such as bacteriophages, plasmids, cosmids, viruses, or retroviruses. In some instances, the vector disclosed herein can be a viral vector, which contains elements derived from a viral genome (naturally occurring or modified). Non-limiting examples of viral vectors include retroviral vectors (e.g., lentiviral vectors or gamma retroviral vectors), adenoviral vectors, adeno-associated viral vectors (AAV), and hybrid vectors (containing components from different viral genomes). Additional examples of viral vectors are provided in U.S. Pat. Nos. 5,698,443, 5,650,309, and 5,827,703, the relevant disclosures of each of which are herein incorporated by reference for the purpose and subject matter referenced herein.

In some embodiments, the zymogens of the present disclosure are expressed in vitro in a cell of interest following introduction of the zymogen-encoding nucleic acid into the cells. In such instances, the host cell undergoes transformation by the nucleic acid construct. According to techniques known in the art, a nucleic acid (e.g., a recombinant DNA construct or a recombinant vector) can be introduced into a cell of interest by various techniques, such as calcium phosphate- or calcium chloride-mediated transfection, electroporation, microinjection, particle bombardment, liposome-mediated transfection, transfection using bacterial bacteriophages, transduction using retroviruses or other viruses, protoplast fusion, *Agrobacterium*-mediated transformation, or other methods. Non-limiting examples of are provided in U.S. Pat. No. 8,241,896, the relevant disclosures of which are herein incorporated by reference for the purpose and subject matter referenced herein.

Cells expressing these nucleic acid constructs may be cultured in vitro using conventional cell culture methods. For example, cells may be grown and maintained at an appropriate temperature and gas mixture (e.g., 37° C., 5% $CO_2$ for mammalian cells) in a cell incubator.

In some embodiments, the zymogens of the present disclosure include a detectable molecule (e.g., a fluorophore). In some embodiments, a nucleic acid construct encoding a zymogen of the present disclosure may be further engineered to express a detectable molecule (e.g., a fluorescent protein).

Pharmaceutical Compositions

When used in vivo, the zymogens of the present disclosure, whether in protein form or in nucleic acid form, may be administered as a pharmaceutically acceptable composition. Such compositions may be sterile compositions comprising the zymogen and a pharmaceutically acceptable carrier.

As used herein, the term "pharmaceutically acceptable carrier" refers to one or more compatible solid or liquid filler, diluents or encapsulating substances which are suitable for administration to a human or other subject contemplated by the disclosure. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers (e.g., antioxidants), gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

The components of the pharmaceutical compositions are combined in a manner that precludes interaction that would substantially impair their desired pharmaceutical efficiency. Moreover, for animal (e.g., human) administration, it will be understood that preparations should meet sterility, pyrogenicity, general safety and purity standards as required by the Food and Drug Administration (FDA) Office of Biological Standards. The zymogens provided herein are generally suitable for administration to humans or mammals.

Mode of Administration

The zymogens of the present disclosure may be administered to a subject in need of the treatment via a suitable route (e.g., intravenous injection or local injection). Similarly, any of the nucleic acid constructs encoding the zymogens can be delivered to a subject in need of the treatment via a suitable route. In some embodiments, the zymogens of the present disclosure can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intramuscularly, intraperitoneally, subcutaneously, subconjunctival, intravesicularlly, mucosally, intrapericardially, intraumbilically, intraocularally, orally, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference).

Treating

Disclosed herein are methods of treating a subject having a disorder characterized by a specific protease, comprising administering to said subject an effective amount of a circular zymogen of the present invention, wherein the proteolytic cleavage site is cleaved by the specific protease. As used herein, the terms "treatment," "treat," and "treating" refer to reversing, alleviating, delaying the onset of, or inhibiting the progress of a "pathological condition" (e.g., a disease, disorder, or condition, including one or more signs or symptoms thereof) described herein. In some embodiments, treatment may be administered after one or more signs or symptoms have developed or have been observed. Treatment may also be continued after symptoms have resolved, for example, to delay or prevent recurrence and/or spread.

In some embodiments, subjects are prophylactically treated. Such prophylactic treatment would involve administration of an effective amount of a circular zymogen of the present disclosure to a subject at risk of developing (or contracting) a disorder characterized by a specific protease.

Effective Amount

The circular zymogens (or compositions thereof) of the present disclosure may be administered in a manner compatible with the dosage formulation. In some embodiments, a subject having or at risk of having a disorder characterized by a specific protease is administered an effective amount of the circular zymogen (or composition thereof). As used herein, the term "effective amount" may refer to an amount sufficient to result in a cytotoxic effect in the target cell or group of target cells (wherein the "target cells" are cells expressing the specific protease) and/or to alleviate symptoms of the disorder characterized by the specific protease. In some embodiments, "an effective amount" is sufficient to slow the progression of the disorder characterized by the symptoms, as measured, for example, by pathogen load, symptom severity etc.

For example, in some embodiments, the specific protease is HIV-1 protease and a circular zymogen is administered to a subject having HIV. In such cases "an effective amount" may be sufficient to alleviate the symptoms of HIV or a secondary infection or condition such as, for example, AIDS. In some embodiments, e.g., wherein the specific protease is HIV-1 protease, "an effective amount" may be sufficient to reduce pathogen load (e.g., HIV viral load) to the extent that the pathogen (e.g., HIV) is no longer detectable in the subject or in samples obtained from the subject.

When administered to a subject, an effective amount of the a circular zymogen or composition of the present disclosure, will depend, of course, on the severity of the disease (e.g. the current pathogen or viral load of the subject), individual patient parameters including age, physical condition, size and weight, concurrent treatment, frequency of treatment, and the mode of administration. These factors are well known to those of ordinary skill in the art and can be addressed with no more than routine experimentation. In some embodiments, a maximum dose is used, that is, the highest safe dose according to sound medical judgment.

Subject

In some embodiments of the present disclosure, the term "subject" refers to a mammal. In some embodiments the subject is a human or human patient. In some embodiments, the subject is an animal (e.g., animal model). In other embodiments the subject is a mouse. Subjects also include animals such as household pets (e.g., dogs, cats, rabbits, ferrets, etc.), livestock or farm animals (e.g., cows, pigs, sheep, chickens, and other poultry), horses such as thoroughbred horses, laboratory animals (e.g., rats, rabbits, etc.), and the like.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Examples

Latent reservoirs thwart a reliable cure for HIV as viremia rebounds upon halting antiretroviral therapy, making HIV infection a chronic illness. The strategy nature devised to enable cellular production of toxic proteins-expression of inactivated, zymogen forms that are proteolytically activated at the site of action-provides a framework to engineer prodrug variants that target HIV infected cells. De novo engineering of zymogens has only achieved limited success. The disclosed zymogens of RNase 1 hold the promise to engender cytotoxicity (e.g., to HIV-infected cells) and could find utility as part of a combinatorial viral eradication therapy.

Herein the design and characterization of HIV protease-activated zymogens of RNase 1 is reported. Herein, the first circular zymogen of RNase 1 is engineered de novo by circular permutation to connect the native N- and C-termini (optionally truncated) with a linker, and intein-mediated cyclization to create a circular zymogen. The linker comprises a protease recognition sequence that allows selective activation of the zymogen by a specific protease. The imposition of strain in the zymogens of the present disclosure yields unprecedented inactivation that is relieved by the action of the specific protease (e.g., HIV-1 protease).

Results

Design of a Circular Zymogen Construct

Circular RNase 1 zymogens were created by intein-mediated cis-splicing with the *Nostoc punctiforme* (Npu) DnaE split intein (Evans et al. *J. Biol. Chem.* 275, 9091-9094; 2000, the relevant disclosures of which are herein incorporated by reference for the purpose and subject matter referenced herein). The Npu intein utilizes a "CFN" N-terminal splice junction. Herein, the "CFQ" sequence that begins at residue 58 of human RNase 1 was utilized. Additionally, the 4-residue C-terminal extension (residues 125-128) of RNase 1 were omitted because they are not important for activity.

Design and Assessment of Glycine (G) Series of Zymogens

Figure 3:
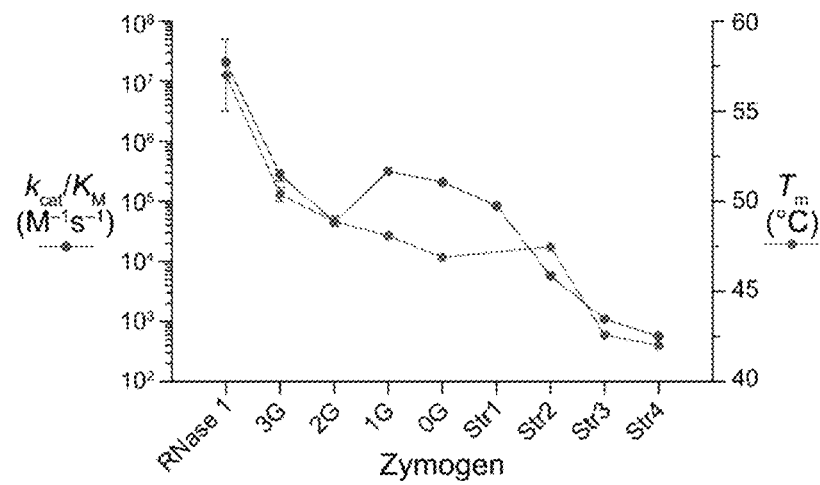
FIG. 3 shows the activity and stability of circular zymogens of RNase 1. Plotting catalytic efficiency ($k_{cat}/K_M$) and thermal stability ($T_m$) of wild-type RNase 1 and a number of zymogens reveals an exponential loss in activity is associated with a linear loss of stability.

Prior to the present disclosure, zymogens (e.g., RNase A zymogens) exhibited modest inactivation (e.g., less than 1,000-fold) suggesting a 14-residue linker would not effectively block the active site of RNase 1. First, a series of zymogens was designed to test this hypothesis by bringing the linker closer to the active site with progressively shorter linkers. Additionally, a substrate identified by phage display that is cleaved efficiently by HIV-1 protease (SGIFLETS (SEQ ID NO: 1)) was employed (Beck et al. (2000) Virology 274, 391-401). This sequence was flanked with varying numbers of glycine residues to create the G series of zymogens (Table 2). A plasmid encoding the intein fragments flanking a circularly permuted RNase 1 connected by the substrate linker directed the expression of the two soluble proteins and another insoluble one corresponding to the intein fragments and the circular RNase 1 (FIG. 2), indicative of intein-mediated cyclization. These zymogens all exhibited roughly two orders-of-magnitude less activity than did wild-type RNase 1, and no trend in inactivation was observed despite a progressive reduction in thermostability (FIG. 3).

Design and Assessment of Strained (Str) Series of Zymogens

The following step was to remove residues from the termini of RNase 1 to bring the linker closer to active site with the intent of imposing strain. Crystallization optimization of RNase 1 revealed that the first 7 N-terminal residues can be removed with only an order of magnitude loss in activity.[18] Lys7 is important for binding the phosphoryl group of the RNA backbone in the $P_2$ subsite.[19, 20] Folding studies of RNase A demonstrated that residues beyond 122 (i.e., 123-128) can be removed without diminishing activity or stability.[21] Hence, truncation was constrained to the first 6 residues on the N-terminus and the final 6 residues on the C-terminus. The terminal residues of the protease substrate are both serine. Removal of the three N-terminal (ΔKES) and two C-terminal (ASV) residues and connecting them with the protease substrate would replace the truncated serine residues. This construct was selected as a starting point for the strained (Str) series of zymogens and further truncated by progressively removing residues 4, 5, and 6 (Table 2). The Str1 zymogen showed a similar, two orders-of-magnitude reduction in activity of that in the glycine series. Further truncations reduced the activity of the zymogens substantially, with a disproportionately smaller reduction in thermostability (Table 4; FIG. 3).

TABLE 4

Activity and stability of RNase 1 and zymogens

| RNase/Zymogen | $k_{cat}/K_M$ (M$^{-1}$s$^{-1}$) | $T_m$ (° C.) |
|---|---|---|
| RNase 1[a] | 2.1 ± 0.2 × 10$^7$ | 57 ± 2 |
| 3G | 2.8 ± 0.6 × 10$^5$ | 50.4 ± 0.4 |
| 2G | 4.6 ± 0.2 × 10$^4$ | 48.9 ± 0.3 |
| 1G | 3.2 ± 0.2 × 10$^5$ | 48.1 ± 0.1 |
| 0G | 2.1 ± 0.2 × 10$^5$ | 46.9 ± 0.2 |
| Str1 | 8.5 ± 0.2 × 10$^4$ | nd |
| Str2 | 5.8 ± 0.05 × 10$^3$ | 47.5 ± 0.1 |
| Str3 | 1.1 ± 0.01 × 10$^3$ | 42.6 ± 0.1 |
| Str4 | 5.7 ± 0.03 × 10$^2$ | 42.0 ± 0.1 | nd, Not determined.
[a]Values are from Johnson et al. Biochemistry 2007, 46 (36), 10308-16.

Assessing Zymogen Activation by HIV-1 Protease

The zymogens exhibiting substantial inactivation, i.e., $k_{cat}/K_M < 10^4$ M$^{-1}$s$^{-1}$, were subjected to activation studies with HIV-1 protease. Proteolysis by the pathogenic protease must be limited to the inactivating linker of the zymogen. It was determined that wild-type RNase 1 is not cleaved by HIV-1 protease (FIG. 4). Next, the zymogens were digested with HIV-1 protease and the final activity was measured. Proteolysis restored near wild-type activity to the Str2-4 zymogens (Table 5). Finally, a continuous assay was developed to measure the $k_{cat}/K_M$ value for HIV-1 protease cleavage of the zymogens (Tables 5 and 6, FIG. 5).

TABLE 5

Properties of Str Series Zymogens. Enzymatic activity ($k_{cat}/K_M$)

| Zymogen | $k_{cat}/K_M$ (activated zymogen) | Relative Activity | $k_{cat}/K_M$ (HIV-1 protease) |
|---|---|---|---|
| Str2 | 6.7 ± 0.08 × 10$^7$ | 11,000 | 3.9 ± 0.3 × 10$^3$ |
| Str3 | 3.2 ± 0.02 × 10$^6$ | 2,800 | 1.3 ± 0.1 × 10$^3$ |
| Str4 | 1.4 ± 0.02 × 10$^7$ | 24,000 | 2.5 ± 0.1 × 10$^3$ |

TABLE 6

Str zymogen kinetic parameters at pH 5.0

| Zymogen | $k_{cat}/K_M$ (M$^{-1}$s$^{-1}$) Inactive | $k_{cat}/K_M$ (M$^{-1}$s$^{-1}$) Activated |
|---|---|---|
| Str2 | 2.9 ± 0.06 × 10$^3$ | 5.2 ± 0.2 × 10$^5$ |
| Str3 | 7.3 ± 0.08 × 10$^2$ | 7.0 ± 0.3 × 10$^5$ |
| Str4 | 9.2 ± 0.3 × 10$^2$ | 2.4 ± 0.4 × 10$^6$ |

Modelling the Structural Basis of Str2 Zymogen Inactivation

The zymogen Str2 possessed the best combination of key attributes: catalytic inactivation, thermostability, and proteolytic activation. Accordingly, the Str2 zymogen was modelled with Rosetta to reveal the structural origins of catalytic inactivation in the zymogen design. The top ten scoring models of four-hundred were examined and it was found that the N-terminal α-helix was nearly intact, whereas the C-terminal β-strand was distorted in each model (FIGS. 6A, 6B, and 7A).

Modelling the Structural Basis of Proteolytic Activation of Str2 by HIV-1 Protease Again, modelling with Rosetta was used to reveal the structural basis of recognition of the inactivating linker by HIV-1 protease. The top ten scoring models of two-hundred were examined and it was found that the N-terminal α-helix and C-terminal β-strand must be completely unfolded to accommodate HIV-1 protease with its flaps closed upon a substrate installed in the linker (FIGS. 6A, 6C, and 7B).

Materials and Methods

Conditions

All procedures were performed in air at ambient temperature (22° C.) and pressure (1.0 atm) unless indicated otherwise.

Protein Expression and Purification

The RNase 1 gene was obtained from a previously reported molecular clone.[26] Intein fragments were obtained from previously described vectors.[27] The circular RNase 1 zymogen construct was initially prepared using the linker sequence from a circularly permuted RNase A zymogen containing the p2/NC cleavage site. PCR was used to prepare five DNA fragments with terminal homology: the pET32b plasmid, NpuC, a C-terminal RNase fragment, an N-terminal RNase fragment, and the NpuN fragment. Gibson assembly was used to combine fragments into the final expression constructs. Modification of the original plasmid was done by producing RNase 1 fragments with PCR by including the new linkers and truncations, and combining these fragments with a plasmid fragment that contained both intein fragments.

Ribonucleases were produced by heterologous expression and purified as previously.[26] All chromatography and assay buffers were treated with DEPC prior to use, with the exception of Tris which was added from ribonuclease-free stocks (Invitrogen).

Zymogens were folded in the presence of 0.5 M arginine·HCl and were purified with additional chromatography on a MonoS column (GE Healthcare) to ensure purity and removal of contaminating ribonucleases. HIV-1 protease was produced by heterologous expression and purified as described previously.[22] Protein purity was confirmed by SDS-PAGE, and concentrations were determined by using the Pierce™ BCA assay kit (ThermoFischer Scientific). HIV-1 protease was also treated with 10 mM DTT at 4° C. for 4 h to inactivate contaminating RNases. The ensuing solution was desalted by passage through a HiTrap® column (GE Healthcare) and did not possess detectable ribonucleolytic activity.

Enzyme Activity Assays

The kinetics of RNA hydrolysis was monitored by the increase in fluorescence intensity of a doubly labeled fluorogenic substrate, 6-FAM-dArUdAdA-6-TAMRA, upon exposure to RNases.[28] Initial ($I_o$) and final ($I_f$) intensities along with linear slopes (m=ΔI/Δt) or the second derivative of quadratic fits (2a=Δ$^2$I/Δt$^2$) were measured and used to calculate the value of $k_{cat}/K_M$. Assays required 10 pM-1 μM to achieve velocities that reached 10% RNA turnover within several minutes. Activated zymogens were prepared for kinetic testing by digesting 50 μM zymogen with 52 nM HIV-1 protease at 37° C. Continuous activation assays were performed with 2.6 nM HIV-1 protease. Fluorescence intensity was measured with a M1000 microplate reader (Tecan) by monitoring emission at 515 nm with excitation at 493 nm. Assays were performed in quadruplicate in a flat, black 96-well plate (Corning). Assay buffers were DEPC-treated and consisted of either 50 mM Tris, pH 7.4, containing NaCl (100 mM) or 50 mM sodium acetate, pH 5.0, containing NaCl (100 mM).

Ribonucleolytic activity was assessed with eq 1 by assaying initial velocities under second-order conditions.

$$\frac{k_{cat}}{K_M} = \frac{\frac{\Delta I}{\Delta t}}{[\text{ribonuclease}](I_f - I_o)} \quad (1)$$

Steady-state kinetic parameters for zymogen cleavage by HIV-1 protease were determined with eq 2 by assaying the increase in ribonucleolytic activity observed upon the addition of the protease.

$$\frac{k_{cat}}{K_M}_{HIV-1\,protease} = \frac{\frac{\Delta^2 I}{\Delta t^2}}{\frac{k_{cat}}{K_M}_{zymogen,activated}[\text{zymogen}][HIV-1\,protease](I_f - I_o)} \quad (2)$$

Values of $k_{cat}/K_M$ at pH 7.4, which is the pH optima of RNase 1,[29] are reported in the main text. These values were also determined at pH 5, the optima of HIV-1 protease, and used as parameters in the fitting of eq 2 (Table 6). Values of $k_{cat}/K_M$ are reported as the mean±SD of quadruplicate measurements.

Thermostability Assays

The thermostability of ribonucleases was determined by differential scanning fluorometry. The thermostability of G series zymogens was determined with a CFX connect RT-PCR machine (Bio-Rad). Samples of 5 μM protein with 1% v/v SYPRO Orange (Sigma-Aldrich) in 25 μL of PBS were heated from 25-95° C. at 1° C./min. Single fluorescent measurements per degree were recorded, and the change in fluorescence per ° C. was calculated with Excel software (Microsoft) by using the equation: $\Delta F_t = F_{t+1} - F_{t-1}$. The maximal change in fluorescence and the 5 flanking measurements above and below were fitted with the Gaussian function built into Prism 6 (Graphpad). Values of $T_m$ are reported as the mean±SD of triplicate measurements.

The thermostability of Str zymogens was determined with a ViiA 7 RT PCR machine (Applied Biosystems). Samples of 30 μg zymogen with 0.6% v/v SYPRO Orange in 20 μL of PBS were heated from 20-96° C. at 1° C./min in steps of 1° C. The value of $T_m$ was determined with the Protein Thermal Shift software (Applied Biosystems) using the Boltzman model and reported as the mean and standard error.

Modelling with Rosetta

Modeling of the Str2 zymogen and its complex with HIV-1 protease were conducted with Rosetta software.[30] RNase 1 from PDB entry 1z7x was extracted from chain A.[25] RNase 1 was circularly permuted at residue 89 to include the linker between the termini. The 15 N-terminal and 12 C-terminal residues were removed so as to be predicted computationally. KIC loop modelling was performed using fragments picked by the Rosetta Server to prepare 400 models of the zymogen linker and proximal residues of the native termini.[31, 32]

Modelling of the complex was conducted in two steps. RosettaDock was employed to dock HIV-1 protease in the closed conformation bound to the "SGIFLETS" (SEQ ID NO: 1) from chain A of PDB entry 6bra into the active-site cleft of the N- and C-terminally truncated structure of RNase 1.[33, 34] Docking models were inspected manually to identify orientations with proximal termini of RNase 1 and the substrate in the active site of HIV-1 protease. Five docking models compatible with a zymogen-protease complex were subjected to further modelling of their loop. The docking model that generated the lowest-energy complex by loop modelling was used to prepare an additional 200 models. The top-10 lowest energy models (Table 7) are shown in FIG. 7.

TABLE 7

Total scores of models calculated by Rosetta

| Model | Str2 (REU) | Complex (REU) |
|---|---|---|
| 1 | −197.697 | −522.837 |
| 2 | −196.236 | −518.158 |
| 3 | −193.333 | −511.494 |
| 4 | −192.159 | −466.197 |
| 5 | −191.876 | −457.239 |
| 6 | −191.655 | −456.408 |
| 7 | −191.556 | −454.677 |
| 8 | −191.252 | −453.330 |
| 9 | −191.203 | −451.303 |
| 10 | −190.923 | −451.246 |

REU = Rosetta Energy Units

Discussion

The mechanism of the zymogen inactivation herein relies on two key strategies: steric occlusion and strain. Roughly two orders-of-magnitude in activity are lost by installing a linker across the active site, as observed with previously-studied circularly permuted RNase A zymogens. Further inactivation was achieved through local installation of strain, which was a violation of design criteria in the previous circularly permuted zymogens that was enabled herein by intein-mediated cyclization.[8] The key catalytic residues are located in secondary structural elements at the termini that are not stabilized by disulfide bonds, unlike the core structure (FIG. 6). Through installation of strain by progressive truncation, the active site residues were perturbed specifically to achieve unprecedented inactivation of a de novo engineered zymogen without compromising global stability. Structural modelling revealed how steric occlusion and strain are operational in the zymogen design herein. The top-10 scoring structures are predicted to be similar in energy, yet conformationally divergent in the linker. This dichotomy suggests that the zymogen linker has a dynamic conformation, but also unambiguously demonstrates that both termini cannot simultaneously adopt the wild-type fold.

Despite the increased proximity of the linker to the active site compared to previous zymogens, the zymogen designs disclosed herein maintained efficient activation. Two-orders-of-magnitude reduction were observed of the second-order rate constant of HIV-1 protease toward the zymogens with respect to a fluorogenic peptide substrate, which is cleaved with a $k_{cat}/K_M$ value of $5.0 \times 10^5$ $M^{-1}s^{-1}$.[22] Herein, the chosen substrate is among the most efficiently hydrolyzed by HIV-1 protease and the activity is reduced to rate constants similar to endogenous substrates when incorporated into zymogens.[23] As indicated by the modelling herein, the loss in catalytic efficiency results from the energetic cost of unfolding the N- and C-terminal structural elements of the zymogen to accommodate the flaps of the protease, HIV-1 protease. Not all proteases employ flaps, and zymogens might be more efficiently activated by other pathogenic proteases like plasmepsins that have an open active-site cleft.

REFERENCES (1) Collaboration, H.-C., Ray, M., Logan, R., Sterne, J. A., Hernandez-Diaz, S., Robins, J. M., Sabin, C., Bansi, L., van Sighem, A., de Wolf, F., Costagliola, D., Lanoy, E., Bucher, H. C., von Wyl, V., Esteve, A., Casbona, J., del Amo, J., Moreno, S., Justice, A., Goulet, J., Lodi, S., Phillips, A., Seng, R., Meyer, L., Perez-Hoyos, S., Garcia de Olalla, P., and Hernan, M. A. (2010) The effect of combined antiretroviral therapy on the overall mortality of HIV-infected individuals, AIDS 24, 123-137.

(2) Chun, T. W., Justement, J. S., Murray, D., Hallahan, C. W., Maenza, J., Collier, A. C., Sheth, P. M., Kaul, R., Ostrowski, M., Moir, S., Kovacs, C., and Fauci, A. S. (2010) Rebound of plasma viremia following cessation of antiretroviral therapy despite profoundly low levels of HIV reservoir: Implications for eradication, AIDS 24, 2803-2808.
(3) Hendrickson, C. J., Pascoe, S. J. S., Huber, A. N., Moolla, A., Maskew, M., Long, L. C., and Fox, M. P. (2018) "My future is bright . . . I won't die with the cause of AIDS": Ten-year patient ART outcomes and experiences in South Africa, J. Int. AIDS Soc. 21, e25184.
(4) Siliciano, R. F., and Greene, W. C. (2011) HIV latency, Cold Spring Harb. Perspect. Med. 1, a007096.
(5) Shirakawa, K., Chavez, L., Hakre, S., Calvanese, V., and Verdin, E. (2013) Reactivation of latent HIV by histone deacetylase inhibitors, Trends Microbiol. 21, 277-285.
(6) Kim, Y., Anderson, J. L., and Lewin, S. R. (2018) Getting the "Kill" into "Shock and Kill": Strategies to eliminate latent HIV, Cell Host Microbe 23, 14-26.
(7) Vocero-Akbani, A. M., Heyden, N. V., Lissy, N. A., Ratner, L., and Dowdy, S. F. (1999) Killing HIV-infected cells by transduction with an HIV protease-activated caspase-3 protein, Nat. Med. 5, 29-33.
(8) Plainkum, P., Fuchs, S. M., Wiyakrutta, S., and Raines, R. T. (2003) Creation of a zymogen, Nat. Struct. Biol. 10, 115-119.
(9) Johnson, R. J., Lin, S. R., and Raines, R. T. (2006) A ribonuclease zymogen activated by the NS3 protease of the hepatitis C virus, FEBS J. 273, 5457-5465.
(10) Turcotte, R. F., and Raines, R. T. (2008) Design and characterization of an HIV-specific ribonuclease zymogen, AIDS Res. Hum. Retroviruses 24, 1357-1363.
(11) Callis, M., Serrano, S., Benito, A., Laurents, D. V., Vilanova, M., Bruix, M., and Ribo, M. (2013) Towards tricking a pathogen's protease into fighting infection: The 3D structure of a stable circularly permuted onconase variant cleaved by HIV-1 protease, PLoS One 8, e54568.
(12) Kanno, A., Yamanaka, Y., Hirano, H., Umezawa, Y., and Ozawa, T. (2007) Cyclic luciferase for real-time sensing of caspase-3 activities in living mammals, Angew. Chem., Int. Ed. 46, 7595-7599.
(13) Butler, J. S., Mitrea, D. M., Mitrousis, G., Cingolani, G., and Loh, S. N. (2009) Structural and thermodynamic analysis of a conformationally strained circular permutant of barnase, Biochemistry 48, 3497-3507.
(14) Evans, T. C., Jr., Martin, D., Kolly, R., Panne, D., Sun, L., Ghosh, I., Chen, L., Benner, J., Liu, X. Q., and Xu, M. Q. (2000) Protein trans-splicing and cyclization by a naturally split intein from the dnaE gene of Synechocystis species PCC6803, J. Biol. Chem. 275, 9091-9094.
(15) Zettler, J., Schutz, V., and Mootz, H. D. (2009) The naturally split Npu DnaE intein exhibits an extraordinarily high rate in the protein trans-splicing reaction, FEBS Lett. 583, 909-914.
(16) Bal, H. P., and Batra, J. K. (1997) Human pancreatic ribonuclease—deletion of the carboxyl-terminal EDST extension enhances ribonuclease activity and thermostability, Eur J Biochem 245, 465-469.
(17) Beck, Z. Q., Hervio, L., Dawson, P. E., Elder, J. H., and Madison, E. L. (2000) Identification of efficiently cleaved substrates for HIV-1 protease using a phage display library and use in inhibitor development, Virology 274, 391-401.
(18) Pous, J., Mallorqui-Fernandez, G., Peracaula, R., Terzyan, S. S., Futami, J., Tada, H., Yamada, H., Seno, M., de Llorens, R., Gomis-Ruth, F. X., and Coll, M. (2001) Three-dimensional structure of human RNase 1 delta N7 at 1.9 Å resolution, Acta Crystallogr. D57, 498-505.
(19) Fontecilla-Camps, J. C., de Llorens, R., le Du, M. H., and Cuchillo, C. M. (1994) Crystal structure of ribonuclease A.d(ApTpApApG) complex. Direct evidence for extended substrate recognition, J. Biol. Chem. 269, 21526-21531.
(20) Fisher, B. M., Ha, J. H., and Raines, R. T. (1998) Coulombic forces in protein-RNA interactions: Binding and cleavage by ribonuclease A and variants at Lys7, Arg10, and Lys66, Biochemistry 37, 12121-12132.
(21) Fujii, T., Ueno, H., and Hayashi, R. (2002) Significance of the four carboxyl terminal amino acid residues of bovine pancreatic ribonuclease A for structural folding, J. Biochem. 131, 193-200.
(22) Windsor, I. W., and Raines, R. T. (2015) Fluorogenic assay for inhibitors of HIV-1 protease with sub-picomolar affinity, Sci. Rep. 5, 11286.
(23) Tozser, J., Blaha, I., Copeland, T. D., Wondrak, E. M., and Oroszlan, S. (1991) Comparison of the HIV-1 and HIV-2 proteinases using oligopeptide substrates representing cleavage sites in Gag and Gag-Pol polyproteins, FEBS Lett. 281, 77-80.
(24) Lomax, J. E., Eller, C. H., and Raines, R. T. (2012) Rational design and evaluation of mammalian ribonuclease cytotoxins, Methods Enzymol. 502, 273-290.
(25) Johnson, R. J., McCoy, J. G., Bingman, C. A., Phillips, G. N., Jr., and Raines, R. T. (2007) Inhibition of human pancreatic ribonuclease by the human ribonuclease inhibitor protein, J. Mol. Biol. 368, 434-449.
(26) Leland, P. A., Staniszewski, K. E., Kim, B. M., and Raines, R. T. (2001) Endowing human pancreatic ribonuclease with toxicity for cancer cells, J. Biol. Chem. 276, 43095-43102.
(27) Shah, N. H., Vila-Perello, M., and Muir, T. W. (2011) Kinetic control of one-pot trans-splicing reactions by using a wild-type and designed split intein, Angew. Chem., Int. Ed. 50, 6511-6515.
(28) Kelemen, B. R., Klink, T. A., Behlke, M. A., Eubanks, S. R., Leland, P. A., and Raines, R. T. (1999) Hypersensitive substrate for ribonucleases, Nucleic Acids Res 27, 3696-3701.
(29) Eller, C. H., Lomax, J. E., and Raines, R. T. (2014) Bovine brain ribonuclease is the functional homolog of human ribonuclease 1, J. Biol. Chem. 289, 25996-26006.
(30) O'Meara, M. J., Leaver-Fay, A., Tyka, M. D., Stein, A., Houlihan, K., DiMaio, F., Bradley, P., Kortemme, T., Baker, D., Snoeyink, J., and Kuhlman, B. (2015) Combined covalent-electrostatic model of hydrogen bonding improves structure prediction with Rosetta, J. Chem. Theory Comput. 11, 609-622.
(31) Gront, D., Kulp, D. W., Vernon, R. M., Strauss, C. E., and Baker, D. (2011) Generalized fragment picking in Rosetta: Design, protocols and applications, PLoS One 6, e23294.
(32) Stein, A., and Kortemme, T. (2013) Improvements to robotics-inspired conformational sampling in rosetta, PLoS One 8, e63090.
(33) Wang, C., Bradley, P., and Baker, D. (2007) Proteinprotein docking with backbone flexibility, J. Mol. Biol. 373, 503-519.
(34) Windsor, I. W., and Raines, R. T. (2018) A substrate selected by phage display exhibits enhanced side-chain hydrogen bonding to HIV-1 protease, Acta Crystallogr. D74, 690-694.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A circular zymogen of ribonuclease 1 (RNase 1) having a truncated C-terminus and a truncated N-terminus that are connected by a bridge that comprises a proteolytic cleavage site,
wherein the truncated C-terminus has at least 4 residues truncated and the truncated N-terminus has 1 to 6 residues truncated.

2. The circular zymogen of claim 1, wherein the circular zymogen of RNase 1 is activated by cleavage of the proteolytic cleavage site by a specific protease.

3. The circular zymogen of claim 2, wherein the specific protease is a pathogen-specific protease.

4. The circular zymogen of claim 2, wherein the specific protease is a disorder-specific protease.

5. The circular zymogen of claim 2, wherein the specific protease is HIV-1 protease.

6. The circular zymogen of claim 1, wherein the total number of residues truncated from the C-terminus and the N-terminus is greater than the total number of residues in the bridge.

7. The circular zymogen of claim 1, wherein the truncated C-terminus has 6 residues truncated and the truncated N-terminus has 3 to 6 residues truncated.

8. The circular zymogen of claim 1, wherein the bridge has 8 residues.

9. The circular zymogen of claim 1, wherein the circular zymogen is inactivated greater than $10^4$-fold relative to the catalytic activity of wild-type RNase 1.

10. The circular zymogen of claim 1, wherein the circular zymogen of RNase 1 is activated by cleavage of the proteolytic cleavage site by a specific protease resulting in a catalytic activity less than 2-fold less than the catalytic activity of wild type RNase 1.

11. The circular zymogen of claim 1, wherein amino acid positions 7-122 of RNase 1 as set forth in SEQ ID NO: 2 are retained in the circular zymogen.

12. The circular zymogen of claim 1, wherein the circular zymogen comprises an active site that comprises histidine-12 and histidine-119 of RNase 1 as set forth in SEQ ID NO: 2.

13. A composition comprising the circular zymogen of claim 1.

14. A pharmaceutical composition comprising the circular zymogen of claim 1.

* * * * *